(12) United States Patent
Fu et al.

(10) Patent No.: US 10,286,002 B2
(45) Date of Patent: May 14, 2019

(54) APPLICATION OF A PHILLYRIN/PHILLYGENININ COMPOSITION IN PREPARING A MEDICINE OR HEALTH CARE PRODUCT FOR ALLEVIATING OR/AND TREATING VIRAL DISEASES, AND MEDICINE OR HEALTH CARE PRODUCT FOR TREATING VIRAL DISEASES

(71) Applicant: Li Fu, Dalian (CN)

(72) Inventors: Li Fu, Dalian (CN); Mingming Lu, Dalian (CN); Qiang Fu, Dalian (CN); Kaiqian Wang, Dalian (CN); Min Hui, Dalian (CN); Zhengxian Liu, Dalian (CN); Yang Liu, Dalian (CN); Shuo Wang, Dalian (CN); Hongying Qu, Dalian (CN); Xiaojing Yu, Dalian (CN); Hailing Wang, Dalian (CN); Xin Gai, Dalian (CN)

(73) Assignee: Li Fu, Dalian (CN)

( * ) Notice: Subject to any disclaimer, the term of this patent is extended or adjusted under 35 U.S.C. 154(b) by 0 days.

(21) Appl. No.: 15/502,000

(22) PCT Filed: Dec. 23, 2014

(86) PCT No.: PCT/CN2014/094710
§ 371 (c)(1),
(2) Date: Feb. 6, 2017

(87) PCT Pub. No.: WO2016/019684
PCT Pub. Date: Feb. 11, 2016

(65) Prior Publication Data
US 2017/0232025 A1    Aug. 17, 2017

(30) Foreign Application Priority Data
Aug. 7, 2014    (CN) .......................... 2014 1 0389232

(51) Int. Cl.
| | | |
|---|---|---|
| *A01N 43/04* | (2006.01) |
| *A61K 31/70* | (2006.01) |
| *A61K 31/7048* | (2006.01) |
| *A61K 31/34* | (2006.01) |
| *A61K 47/40* | (2006.01) |

(52) U.S. Cl.
CPC .......... *A61K 31/7048* (2013.01); *A61K 31/34* (2013.01); *A61K 47/40* (2013.01)

(58) Field of Classification Search
None
See application file for complete search history.

(56) References Cited

FOREIGN PATENT DOCUMENTS

| CN | 1748776 A | 3/2006 |
|---|---|---|
| CN | 102210837 A | 10/2011 |

OTHER PUBLICATIONS

Wen et al. J. Med. Plant. Res. ((2010), vol. 4(14), pp. 1455-1458.*
Ye et al. Eur. J. Drug Metab Pharmacokinet (2013), vol. 38, pp. 201-207.*
Thakur et al. Pharmacogn. Rev. (2011), vol. 5(9), pp. 48-54.*
Sedlak et al. Chromatographia Supplement (2008), vol. 68, S35-S41.*
Piao XL, et al., "Lignans From the Fruits of Forsythia Suspensa", Bioorg Med Chem Lett., Mar. 15, 2008, 1 page (Abstract), vol. 18, No. 6.
Deng, L. et al., "Forsythoside A Controls Influenza A Virus Infection and Improves the Prognosis by Inhibiting Virus Replication in Mice", Molecules, 2016, pp. 1-11, vol. 21, No. 524.

* cited by examiner

*Primary Examiner* — Patrick T Lewis
(74) *Attorney, Agent, or Firm* — Greer, Burns & Crain, Ltd.

(57) ABSTRACT

The present invention discloses a new application of a composition of phillyrin and phillygeninin in the preparation of drugs for alleviating or/and treating viral diseases. Experiments prove that the composition of phillyrin and phillygeninin has significant treatment effects on viral influenza and pneumonia, as well as on respiratory syncytial viruses, enteroviruses, herpes zoster simplex viruses, Coxsackie viruses, and the like. This composition is characterized by quick action and less toxic and side effects, and thus is an antiviral drug and health product with safety, high efficiency, stability and simple preparation process, and is suitable for industrial production and easy to promote. The present invention provides a new drug, health product and raw material for preventing and treating various viral diseases.

6 Claims, No Drawings

APPLICATION OF A PHILLYRIN/PHILLYGENININ COMPOSITION IN PREPARING A MEDICINE OR HEALTH CARE PRODUCT FOR ALLEVIATING OR/AND TREATING VIRAL DISEASES, AND MEDICINE OR HEALTH CARE PRODUCT FOR TREATING VIRAL DISEASES

This application is U.S. National phase application corresponding to PCT/CN2014/094710 which was assigned an international filing date of Dec. 23, 2014 and associated with publication WO 2016/019684 and which claims priority to Chinese Application 201410389232.0 filed on Aug. 7, 2014, the disclosures of which are expressly incorporated herein.

TECHNICAL FIELD

The present invention belongs to the field of pharmaceutical chemistry, and in particular to a phillyrin/phillygeninin composition or mixture and its use in the preparation of drugs or health products for alleviating or/and treating viral diseases.

BACKGROUND ART

Influenza is one of acute and viral respiratory infectious diseases which are seriously harmful to human health. Since the 21st century, the prevalence of SARS, virus H5N1 and influenza virus type A H1N1 bring great harms to human beings. At present, there are still no natural drugs capable of effectively treating viral influenza and pneumonia in the world.

Fructus Forsythiae is dried fruits of Forsythia suspensa (Thunb.) Vahl (Oleaceae), which is mainly grown in Henan, Shanxi, Shanxi, Shandong provinces and other places in China, as well as Hubei, Hebei, Sichuan and Gansu provinces. Forsythiae is commonly used for treating diseases of acute wind-heat common cold, carbuncle and sore, tuberculous lymphadenitis, urinary tract infection, etc. The major components of Forsythia suspensa include phillyrin and phillyrin aglycone (also known as phillygeninin), and the structure of the two components are represented by the following formulae.

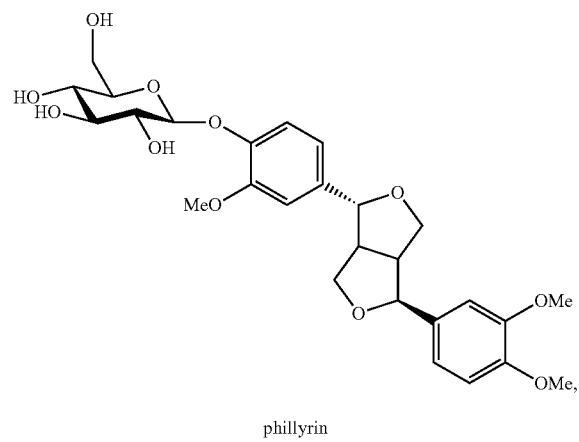

phillyrin

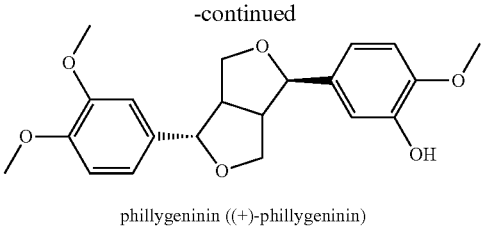

phillygeninin ((+)-phillygeninin)

Phillyrin, as a major component of Forsythia suspensa, has antiviral, antibacterial, antioxidant, free radical scavenging and other pharmacological effects. Phillygeninin, also known as a major active component of Forsythia suspensa, has antioxidant, blood lipid lowering, free radical scavenging, bacteriostasis, anti-tumor and anti-inflammatory effects. The published literatures were mainly directed to study on the antiviral pharmacological effects of Forsythia suspensa extracts containing unknown components and several known components, and phillyrin single component. However, the antiviral pharmacological effects of the phillygeninin/phillyrin composition and the phillygeninin single component were not studied yet.

SUMMARY OF THE INVENTION

For the existing technical problems in treatment, prevention or alleviation of viral diseases, an object of the present invention is to provide an application of a phillyrin/phillygeninin composition in the preparation of drugs or health products for alleviating or/and treating viral diseases. The phillyrin/phillygeninin composition of the present invention has good performance and efficacy in alleviating or/and treating viral diseases, and provides a new way to develop new drugs for alleviating or/and treating viral diseases, that is, providing a new approach for the drugs or health food for alleviating, conditioning and treating viral diseases.

In order to achieve the above object, on one hand, the present invention provides applications of a phillyrin/phillygeninin composition in the preparation of drugs or health products for alleviating or/and treating viral diseases.

Wherein, the viral diseases are those caused by influenza viruses, parainfluenza viruses, Coxsackie virus CoxA16, respiratory syncytial viruses (RSV), herpes zoster simplex virus HSV-I, herpes zoster simplex virus HSV-II, herpes zoster simplex virus CVB3, adenovirus ADV or enterovirus EV71, particularly caused by viral influenza, pneumonia and respiratory infectious diseases caused by influenza viruses, parainfluenza viruses, Coxsackie virus CoxA16 and respiratory syncytial viruses (RSV).

In the process of screening natural active components that are effective in alleviating or/and treating viral influenza, pneumonia and respiratory infectious diseases, the inventor found that the phillyrin/phillygeninin composition has a powerful effect on inhibition of viral influenza and pneumonia, with the effectiveness remarkably better than phillyrin or phillygeninin used alone.

Wherein, the weight ratio of phillyrin to phillygeninin in the phillyrin/phillygeninin composition is 80-98:2-20, preferably 90-98:2-10, more preferably 98:2.

Specifically, the phillyrin/phillygeninin composition further includes a pharmaceutically acceptable carrier.

Such pharmaceutically acceptable carrier is generally considered by healthcare professionals to be able to achieve this purpose and serve as a non-active component of drugs. The corpus of the pharmaceutically acceptable carriers can be found in reference books, such as, Handbook of Pharmaceutical excipients, 2nd Edition, edited by A. Wade and P. J. Weller, published by American Pharmaceutical Association, Washington and the Pharmaceutical Press, London, 1994.

Particularly, the carrier includes an excipient, such as starch and water; a lubricant, such as magnesium stearate; a disintegrant, such as microcrystalline cellulose; a filler, such as lactose; a binder, such as pregelatinized starch and dextrin; a sweetener; an antioxidant; an antiseptic, a flavoring, an essence, etc.

Specifically, the drug of the present invention is present in forms of tablets, capsules, pills, powders, granules, syrups, solutions, emulsions, injections, sprays, aerosols, gels, creams, cataplasms, rubber plasters or patches.

Wherein, the weight ratio of the phillyrin and phillygeninin in the phillyrin/phillygeninin composition to the pharmaceutically acceptable carrier is 1:1 to 1:100, preferably 1:100, more preferably 1:5, still more preferably 1:2, and even still more preferably 1:1.

Specifically, the content of the phillyrin/phillygeninin composition is equal to or greater than 80% (i.e. ≥80%), preferably ≥85%, more preferably ≥88%, still more preferably ≥90%, and even still more preferably ≥99%.

Specifically, the weight ratio of phillyrin and phillygeninin in the phillyrin/phillygeninin composition is 2-98:98-2, preferably 80:20 or 20:80, more preferably 90:10 or 10:90, and still more preferably 98:2 or 2:98.

Wherein, the phillyrin/phillygeninin composition is formed by phillyrin and phillygeninin in form of monomers, or is a phillygeninin-phillyrin extract composition prepared by heat extraction using a solvent, or is a phillygeninin-phillyrin-cyclodextrin composition formed by combining phillygeninin and phillyrin with cyclodextrin or a cyclodextrin derivative.

Specifically, the phillygeninin-phillyrin-cyclodextrin composition is a mixture formed by mixing phillygeninin and phillyrin with α-cyclodextrin, β-cyclodextrin or γ-cyclodextrin or a derivative thereof, or a composite formed by phillygeninin, phillyrin, and α-cyclodextrin, β-cyclodextrin or γ-cyclodextrin or a derivative thereof via physical or chemical treatment.

Wherein, the ratio of the total weight of phillyrin and phillygeninin in the phillygeninin-phillyrin-cyclodextrin composition to the weight of the cyclodextrin or cyclodextrin derivative is 1:1-50.

Particularly, the cyclodextrin is α-cyclodextrin, β-cyclodextrin or γ-cyclodextrin; the cyclodextrin derivative is hydroxyethyl β-cyclodextrin, 2,6-dimethyl β-cyclodextrin, 2,3,6-trimethyl β-cyclodextrin, 2,6-diethyl β-cyclodextrin, 2,3,6-diethyl-βcyclodextrin, maltosyl β-cyclodextrin or sulfobutyl ether β-cyclodextrin, p-toluenesulfonyl chloride (p-TsCl) substituted β-cyclodextrin, 6-position substituted β-CD p-toluenesulfonate (β-cyclodextrin-6-OTs), 2-oxyhydro xypropyl-β-cyclodextrin, 2-position monosubstituted p-toluenesulfonate (β-cyclodextrin-2-OTs), β-cyclodextrin p-toluenesulfonate (Tosyl-β-CD), and a star-shaped macromolecule of β-cyclodextrin PCL-(Tos)7-β-CD.

Wherein, the phillyrin-phillygeninin extract composition is prepared according to the following method:
1) reflux-extracting leaves or fruits of Forsythia suspensa using a solvent under heating for 2~3 times, 2-4 hours each time;
2) concentrating the extracted liquid, and then allowing the concentrate to stand for precipitation, thereby obtaining a crude mixture of phillygeninin and phillyrin;
3) dissolving the crude mixture of phillygeninin and phillyrin in a solvent, allowing the same to stand for crystallization, to obtain a mixture of phillygeninin and phillyrin;
4) subjecting the mixture of phillygeninin and phillyrin to recrystallization using a solvent, to obtain a phillygeninin-phillyrin extract.

Specifically, the solvent in step 1), 3) and 4) is methanol, ethanol, acetone, methanol solution comprising water or ethanol solution comprising water.

More specifically, the mass percent concentration of the methanol solution is 70-95%; the mass percent concentration of the ethanol solution is 70-95%.

Wherein, in step 2), the standing for precipitation operation is carried out at room temperature, preferably 10-35° C., more preferably 20-25° C.; the standing time is 1-48 hours; in step 2), the ratio of the volume of the concentrated extraction liquid to the volume of the original extraction liquid is 0.1-0.5:1.

Specifically, in step 4), the recrystallization is carried out at room temperature, preferably 10-35° C., more preferably 20-25° C.

Another aspect of the present invention is to provide a drug or health product for alleviating or/and treating viral diseases, containing phillyrin and phillygeninin.

Wherein, the weight ratio of phillyrin to phillygeninin is 80-98:2-20, preferably 90-98:2-10, more preferably 98:2.

Specifically, the drug or health product consists of a phillyrin/phillygeninin composition and a pharmaceutically acceptable carrier.

Wherein, the ratio of the total weight of phillyrin and phillygeninin in the phillyrin/phillygeninin composition to the weight of the pharmaceutically acceptable carrier is 1:1 to 1:100, preferably 1:100, more preferably 1:5, still more preferably 1:2, and even still more preferably 1:1.

Specifically, the ratio of the weight of the phillygeninin/phillyrin composition to the total weight of the drug or health product is 0.01-10:100, preferably 0.1-10:100, more preferably 1-10:100.

Specifically, the drug exists in form of tablets, capsules, pills, powders, granules, syrups, solutions, emulsions, injections, sprays, aerosols, gels, creams, cataplasms, rubber plasters or patches.

Specifically, the drug or health product further includes one or more of Herba taraxaci extract, Radix isatidis extract, Flos lonicera extract, Rhizoma anemarrhena extract, Radix scrophularia extract, Spica prunella extract, Rhizoma phragmites extract, and Herba lophatheri extract, Fructus gardeniae extract, Bulbus fritillariae cirrhosae extract, Leaf of Chinese holly extract, and Herba houttuyniae extract.

The drug can be prepared into different pharmaceutical preparations, such as tablets, capsules, pills, powders, granules, syrups, solutions, emulsions, injections, sprays, aerosols, gels, creams, cataplasms, rubber plasters or patches, by using a commonly known method in the art.

The present invention further provides a method for treating viral influenza and pneumonia diseases, including administering a therapeutically effective amount of a pharmaceutical composition of phillygeninin and phillyrin to a patient, the therapeutically effective dosage is 0.1-50 mg/kg·d, preferably 0.3-30 mg/kg·d, more preferably 0.5-10 mg/kg·d.

Unless otherwise indicated, the term "therapeutically effective dosage" used herein is the dosage of the drug desired for producing the efficacy; the "therapeutically effective dosage" may be adjusted and varied, finally determined by the medical staff, depending on the factors considered, including the route of administration, the property of preparation, recipient's weight, age and other general conditions, and the nature and severity of diseases to be treated.

Compared with the prior art, the present invention has the following distinct advantages:

The preparation method of the phillyrin/phillygeninin composition of the present invention is simple and suitable for industrial production, the composition has remarkable effectiveness on resistance to various viral diseases such as influenza and pneumonia, and the antiviral effectiveness is better than that of phillyrin and phillygeninin used alone, and also better than oseltamivir phosphate (Tamiflu) that is the latest antiviral drug in clinics. Furthermore, it is also found that the phillyrin/phillygeninin composition has effectiveness on resistance to other viruses, exhibits a significantly inhibitory effect on Coxsackie virus CoxA16, respiratory syncytial viruses (RSV), herpes zoster simplex virus HSV-I, herpes zoster simplex virus HSV-II, herpes zoster simplex virus CVB3, adenovirus ADV and enterovirus EV71, and can be used for the treatment of diseases caused by the above mentioned viruses, such as influenza and pneumonia, herpes zoster, myocarditis, hand-foot-and-mouth disease, upper respiratory tract infection, capillary bronchitis, skin rashes, and meningitis. Therefore, the present invention may be prepared into high-efficacy natural drugs or health food for alleviating or/and treating diseases such as viral influenza and pneumonia, herpes zoster, myocarditis, hand-foot-and-mouth disease, upper respiratory tract infection, capillary bronchitis, skin rashes, meningitis and other diseases, thus opening up a new field for the use of Forsythia suspensa medicinal material.

1. The phillyrin/phillygeninin composition of the present invention has effectiveness on resistance to influenza viruses and pneumonia viruses, and the effectiveness is significantly better than that of phillyrin and phillygeninin used alone; phillyrin and phillygeninin are used in combination at a specified ratio to give a synergistic effect;
2. The phillyrin/phillygeninin composition of the present invention has an inhibitory effect on Coxsackie virus CoxA16, respiratory syncytial viruses (RSV), herpes zoster simplex virus HSV-I, herpes zoster simplex virus HSV-II, herpes zoster simplex virus CVB3, adenovirus ADV, enterovirus EV71 and other viruses; the phillyrin/phillygeninin composition can be used for the treating the diseases caused by the abovementioned viruses, such as influenza and pneumonia, herpes zoster, myocarditis, hand-foot-and-mouth disease, upper respiratory tract infection, capillary bronchitis, skin rashes, and meningitis;
3. The phillyrin/phillygeninin composition of the present invention has significant effects on inhibition to inflammations caused by viruses and enhancement of patient's immunity; the phillyrin/phillygeninin composition has remarkable pharmacological effect on inhibition to viral influenza and pneumonia, is strongly effective in the alleviation, conditioning and treatment of viral influenza and pneumonia, has quick action, less toxic or side effects and good safety, is suitable for long-term administration, and has good medicinal prospects;
4. The raw material of the product of the prevent invention is abundant, low in price and safe for clinical application, the preparation process is simple, and the product has various forms and small dose, and is easy to use and thus easy to promote;
5. The phillyrin/phillygeninin composition of the present invention may be prepared from monomer components in quantitative combination, may also be prepared by extracting Fructus Forsythiae, or a composite of the phillyrin/phillygeninin composition and α-cyclodextrin or β-cyclodextrin or γ-cyclodextrin, or a cyclodextrin derivative, and may further be a composite of the phillyrin/phillygeninin composition and other active components (such as one or more of Herba taraxaci extract, Radix isatidis extract, Flos lonicera extract, Rhizoma anemarrhena extract, Radix scrophularia extract, Spica prunella extract, Rhizoma phragmites extract, and Herba lophatheri extract, Fructus gardeniae extract, Bulbus fritillariae cirrhosae extract, Leaf of Chinese holly extract, and Herba houttuyniae extract), thereby preparing a compound medicine for treating viral influenza, pneumonia and other viral diseases.

DETAILED DESCRIPTION OF THE INVENTION

The advantages of the formulations of the present invention are further described below by way of specific embodiments. These examples are merely exemplary and are not intended to limit the scope of the invention. It should be understood by those skilled in the art that modifications or alterations to details and forms of the technical solution of the present invention may be made without departing from the concept and usage scope of the formulations of the present invention; however, all these modifications and alterations fall within the scope of the present invention.

Examples 1-4 Preparation of the Phillyrin/Phillygeninin Composition

Two monomer component powders, i.e., Phillyrin and phillygeninin, were separately weighted to mix according to the weight ratio shown in Table 1, to prepare a phillyrin/phillygeninin composition; the phillyrin monomer was manufactured by Dalian Fusheng Natural Drug Development Co., Ltd.; the purity thereof was determined to be 99.5%, determined by HPLC equipped with both UV detector and evaporative light-scattering detector (ELSD) using area normalization method, and the content thereof was calibrated and confirmed to be 99.5% with phillyrin standard available from China Pharmaceutical and Biological Products for content determination; phillygeninin was manufactured by Dalian Fusheng Natural Drug Development Co., Ltd., the purity thereof was determined to be 99.1%, determined by HPLC equipped with both UV detector and evaporative light-scattering detector (ELSD) using area normalization method

TABLE 1

Raw material ratio table for phillyrin/phillygeninin compositions of Examples 1-4

| Example No | weight ratio | |
|---|---|---|
| | phillyrin | phillygeninin |
| Example 1 | 98 | 2 |
| Example 2 | 80 | 20 |
| Example 3 | 90 | 10 |
| Example 4 | 95 | 5 |

Examples 5-24 Preparation of the Phillyrin/Phillygeninin Composition

The phillyrin/phillygeninin composition prepared in Example 1-4 was taken to be prepared into a composition comprising cydodextrin according to the weight ratio shown in Table 2 by using the following method: (1) directly adding to a cydodextrin solution, or (2) directly adding to a cydodextrin solution and well stirring for 1-24 h, (3) directly adding to a cydodextrin solution and heating for 10-120 min, (4) directly adding to a cydodextrin solution and performing ultrasonic treatment for 120 min, (5) directly grinding together with cydodextrin powder for 10-120 min, (6) mixing the phillyrin/phillygeninin composition well with the cydodextrin powder and sieving the mixture; (7) directly adding to a cydodextrin derivative solution, or (8) directly adding to a cydodextrin derivative solution and well stirring for 1-24 h, (9) directly adding to a cydodextrin derivative solution and heating for 10-120 min, (10) directly adding to a cydodextrin derivative solution and performing ultrasonic treatment for 10-120 min, (11) directly grinding together with cydodextrin derivative powder for 10-120 min, (12) mixing well with cydodextrin derivative powder and sieving the mixture.

Example 25 Preparation of the Phillyrin and Phillygeninin Composition 10 kg of 95% (n/m) ethanol was added to 1 kg of dried leaves of Forsythia suspensa, the mixture was reflux-extracted under heating twice for 2 h each time, the extracted liquid was filtered, the filtrate was concentrated under vacuum to ½ of the original volume, and was allowed to stand for precipitating at 25° C. for 1 h to separate out precipitates; the precipitates were dissolved with methanol for recrystallization, and precipitates were separated out; the above process was repeated for recrystallization with methanol to obtain an amorphous powder of a phillyrin/phillygeninin composition, with the contents of phillyrin and phillygeninin being 98% and 2% respectively, as determined by HPLC.

TABLE 2

Raw material ratio and preparation method of Examples 5-24

| Example No. | phillyrin/phillygeninin composition (g) | cyclodextrin or cyclodextrin derivatives (g) | preparation method |
|---|---|---|---|
| Example 5 | 100(98:2) | 100 | (1) directly adding cydodextrin solution |
| Example 6 | 100(80:20) | 10000 | (2) stirring for 1 h |
| Example 7 | 100(90:10) | 500 | (5) heating for 10 min |
| Example 8 | 100(95:5) | 1000 | (4) ultrasonically treating for 10 min |
| Example 9 | 100(98:2) | 2000 | (5) grinding with cydodextrin powder for 10 min |
| Example 10 | 100(98:2) | 3000 | (6) well mixing with the cydodextrin powder and sieving for 10 min |
| Example 11 | 100(98:2) | 4000 | (1) directly adding cydodextrin solution |
| Example 12 | 100(98:2) | 3500 | (2) stirring for 12 h |
| Example 13 | 100(98:2) | 4500 | (3) heating for 120 min |
| Example 14 | 100(98:2) | 1500 | (4) ultrasonically treating for 120 min |
| Example 15 | 100(98:2) | 100 | (7) directly adding cydodextrin derivative solution |
| Example 16 | 100(80:20) | 10000 | (8) stirring for 1 h |
| Example 17 | 100(90:10) | 500 | (9) heating for 10 min |
| Example 18 | 100(95:5) | 1000 | (10) ultrasonically treating for 10 min |
| Example 19 | 100(98:2) | 2000 | (11) grinding with cydodextrin derivative for 10 min |
| Example 20 | 100(98:2) | 3000 | (12) well mixing with cydodextrin derivative and sieving for 10 min |
| Example 21 | 100(98:2) | 4000 | (1) directly adding |
| Example 22 | 100(98:2) | 3500 | (2) stirring for 12 h |
| Example 23 | 100(98:2) | 4500 | (5) heating for 120 min |
| Example 24 | 100(98:2) | 1500 | (6) ultrasonically treating for 120 min |

The excepients used in Examples 5-24 was illustrated by using β-cyclodextrin as an example, other cyclodextrins and cyclodextrin derivatives were also applicable to the present invention, such as 1) β-hydroxyethyl cyclodextrin, 2) hydroethyl β-cyclodextrin, 3) 2,6-dimethyl β-cyclodextrin, 4) 2,3,6-trimethyl β-cyclodextrin, 5) 2,6-diethyl β-cyclodextrin, 6) 2,3,6-triethyl β-cyclodextrin, 7) maltosyl β-cyclodextrin, 8) sulfobutyl ether β-cyclodextrin, 9) p-toluenesulfonyl chloride (p-TsCl) substituted β-cyclodextrin, 10) 6-position substituted β-CD p-toluenesulfonate (β-cyclodextrin-6-OTs), 11) 2-oxy-hydroxypropyl-β-cyclodextrin, 12) 2-position monosubstituted p-toluenesulfonate (β-cyclodextrin-2-OTs), 13) β-cyclodextrin p-toluenesulfonate (Tosyl-β-CD), and 15) a star-shaped macromolecule of β-cyclodextrin PCL-(Tos)7-β-CD.

Example 26 Preparation of the Phillyrin and Phillygeninin Composition 10 kg of methanol was added to 1 kg of dried fruits of Forsvthia suspensa, the mixture was reflux-extracted under heating three times for 4 h each time, the extracted liquid was filtered, the filtrate was concentrated under vacuum to 1/10 of the original volume, and was allowed to stand at 20° C. for 48 h to separate out precipitates; the precipitates were dissolved with ethanol for recrystallization, and precipitates were separated out; the above process was repeated for recrystallization with ethanol to obtain an amorphous powder of a phillyrin/phillygeninin composition, with the contents of phillyrin and phillygeninin being 95% and 4% respectively.

Example 27 Preparation of the Phillyrin and Phillygeninin Composition 10 kg of 70% (m/m) methanol was added to 1 kg of dried leaves of Forsvthia suspensa, the mixture was reflux-extracted under heating there times for 3 h each time; the extracted liquid was filtered, the filtrate was concentrated under vacuum to ⅓ of the original volume, and was allowed to stand at room temperature for 2 h to separate out precipitates; the precipitates were dissolved with 90% methanol for recrystallization, and precipitates were separated out; the above process was repeated for recrystallization with methanol to obtain an amorphous powder of a phillyrin/phillygeninin composition, with the contents of phillyrin and phillygeninin being 88% and 2% respectively.

Example 28 Preparation of the Phillyrin and Phillygeninin Composition 10 kg of anhydrous ethanol was added to 1 kg of dried fruits of Forsvthia suspensa, the mixture was reflux-extracted under heating twice for 4 h each time; the extracted liquid was filtered, the filtrate was concentrated under vacuum to ¼ of the original volume, and was allowed to stand at room temperature for 24 h to separate out precipitates; the precipitates were dissolved with acetone for recrystallization, and precipitates were separated out; the above process was repeated for recrystallization with acetone to obtain an amorphous powder of phillyrin/phillygeninin composition, with the contents of phillyrin and phillygeninin being 90% and 6% respectively.

Example 29 Preparation Of the Phillyrin and Phillygeninin Composition 10 kg of acetone was added to 1 kg of dried leaves of Forsvthia suspensa; the mixture was reflux-extracted three times for 3 h each time; the extracted liquid was filtered, the filtrate was concentrated under vacuum to ⅓ of the original volume and was allowed to stand at room temperature for 10 h to separate out precipitates; the precipitates were dissolved with 70% ethanol for recrystallization, and precipitates were separated out; the above process was repeated for recrystallization with 70% ethanol to obtain an amorphous powder of a phillyrin/phillygeninin composition, with the contents of phillyrin and phillygeninin being 80% and 5% respectively.

Example 30 Preparation of the Phillyrin and Phillygeninin Composition Tablets The phillyrin/phillygeninin composition tablets were prepared according to the following mass ratio:

| | |
|---|---|
| phillyrin/phillygeninin composition (the weight ratio thereof was 98:2) | 500 g |
| starch | 480 g |
| talc powder | 1% (10 g) |
| magnesium stearate | 1% (10 g) |

According to the above ratio, the phillyrin/phillygeninin composition prepared in example 1 was mixed well with starch, and then the mixture was prepared into granules; talc and magnesium stearate were added and mixed well, and the mixture was compressed into 10000 tablets.

Example 31 Preparation of the Phillyrin/Phillygeninin Composition Granules

The phillyrin/phillygeninin composition granules were prepared according to the following mass ratio:

| | |
|---|---|
| phillyrin/phillygeninin composition (the weight ratio thereof was 98:2) | 100 g |
| microcrystalline cellulose | 10000 g |

According to the above ratio, the phillyrin/phillygeninin composition prepared in example 1 was mixed well with microcrystalline cellulose, and then the mixture was prepared into granules; the granules were bagged to form 10000 bags.

Example 32 Preparation of the Phillyrin/Phillygeninin Composition Capsules

The phillyrin/phillygeninin composition capsules were prepared according to the following mass ratio:

| | |
|---|---|
| phillyrin/phillygeninin composition (the weight ratio thereof was 98:2) | 250 g |
| starch | 2500 g |

According to the above ratio, the phillyrin/phillygeninin composition prepared in example 1 was mixed well with starch, and then the mixture was prepared into capsules to form 10000 capsules.

EXAMPLES 33-36 PREPARATION OF THE PHILLYRIN/PHILLYGENININ COMPOSITION CAPSULES

In examples 33-36, the phillyrin/phillygeninin compositions were mixed well with starch according to the weight ratio shown in Table 3, and then the mixture was prepared into capsules to form 10000 capsules for each example.

TABLE 3

| Example No. | Raw material (composition of phillygeninin and phillyrin, g) | Pharmaceutic adjuvant (starch, g) | Weight ratio of the raw material to the pharmaceutic adjuvant |
|---|---|---|---|
| Example 33 | 500 (98:2) | 500 | 1:1 |
| Example 34 | 50 (80:20) | 5000 | 1:100 |
| Example 35 | 250 (90:10) | 2500 | 1:10 |
| Example 36 | 250 (95:5) | 5000 | 1:20 |

The materials in the table can be replaced with the composition of phillygeninin and phillyrin prepared in examples 5-29.

Examples 37-40 Preparation of the Phillyrin/Phillygeninin Composition Granules In examples 37-30, the phillyrin/phillygeninin composition was mixed well with microcrystalline cellulose according to the weight ratios shown in Table 4 respectively, and then the mixture was prepared into granules, the granules were bagged to form 10000 bags.

TABLE 4

| Example No. | Raw material (composition of phillygeninin and phillyrin, g) | Pharmaceutic adjuvant (microcrystalline cellulose, g) | Weight ratio of the raw material to the pharmaceutic adjuvant |
|---|---|---|---|
| Example 37 | 1000 (98:2) | 1000 | 1:1 |
| Example 38 | 250 (80:20) | 25000 | 1:100 |
| Example 39 | 2500 (90:10) | 25000 | 1:10 |
| Example 30 | 2500 (95:5) | 50000 | 1:20 |

The raw materials in the table can be replaced with the composition of phillygeninin and phillyrin prepared in examples 5-29.

Example 41 Preparation of the Phillyrin/Phillygeninin Composition Tablets

The phillyrin/phillygeninin composition tablets were prepared according to the following mass ratio:

| | |
|---|---|
| phillyrin/phillygeninin composition (the weight ratio thereof was 98:2) | 500 g |
| starch | 380 g |
| Herba taraxaci extract | 100 g |
| Talc powder | 1% (10 g) |
| magnesium stearate | 1% (10 g) |

According to the above ratio, the phillyrin/phillygeninin composition was mixed well with the above extract powder, and then as mixed well with starch, the mixture was prepared into granules, talc powder and magnesium stearate were added and mixed well, and then the mixture was compressed into 10000 tablets. Wherein, the phillyrin/phillygeninin composition in the present example can be replaced with the composition of phillygeninin and phillyrin prepared in examples 5-29.

Example 42 Preparation of the Phillyrin/Phillygeninin Composition Granules

The phillyrin/phillygeninin composition granules were prepared according to the following mass ratio:

| | |
|---|---|
| phillyrin/phillygeninin composition (the weight ratio thereof was 98:2) | 250 g |
| Radix isatidis extract | 250 g |
| Flos lonicera extract | 250 g |
| microcrystalline cellulose | 24500 g |

According to the above ratio, the phillyrin/phillygeninin composition was mixed well with the above extract powder, and then mixed well with microcrystalline cellulose, the mixture was prepared into granules; the granules were bagged to form 10000 bags. Wherein, the phillyrin/phillygeninin composition in the present example can be replaced with the composition of phillygeninin and phillyrin prepared in examples 5-29.

Example 43 Preparation of the Phillyrin/Phillygeninin Composition Capsules

The phillyrin/phillygeninin composition granules were prepared according to the following mass ratio:

| | |
|---|---|
| phillyrin/phillygeninin composition (the weight ratio thereof was 98:2) | 250 g |
| Fructus gardeniae extract | 250 g |
| Bulbus fritillariae cirrhosae extract | 250 g |
| Leaf of Chinese holly extract | 250 g |
| starch | 1000 g |

According to the above ratio, the phillyrin/phillygeninin composition was mixed well with the above extract powder, and then mixed well with starch, and the mixture was prepared into capsules to form 10000 capsules. Wherein, the phillyrin/phillygeninin composition in the present example can be replaced with the composition of phillygeninin and phillyrin prepared in examples 5-29.

Example 52 Preparation of the Phillyrin/Phillygeninin Composition Tablets

The phillyrin/phillygeninin composition tablets were prepared according to the following mass ratio:

| | |
|---|---|
| phillyrin/phillygeninin composition (the weight ratio thereof was 80:20) | 500 g |
| starch | 480 g |
| Rhizoma anemarrhena extract | 500 g |
| talc powder | 1% (10 g) |
| magnesium stearate | 1% (10 g) |

According to the above ratio, the phillyrin/phillygeninin composition was mixed well with the above extract powder, and then mixed well with starch, the mixture was prepared into granules; talc and magnesium stearate were added and mixed well; the mixture was compressed into 10000 tablets. Wherein, the phillyrin/phillygeninin composition in the present example can be replaced with the composition of phillygeninin and phillyrin prepared in examples 5-29.

Example 53 Preparation of the Phillyrin/Phillygeninin Composition Granules

The phillyrin/phillygeninin composition granules were prepared according to the following mass ratio:

| | |
|---|---|
| phillyrin/phillygeninin composition (the weight ratio thereof was 90:10) | 1000 g |
| Radix scrophularia extract | 500 g |
| Herba lophatheri extract | 500 g |
| microcrystalline cellulose | 10000 g |

According to the above ratio, the phillyrin/phillygeninin composition was mixed well with the above extract powder, and then mixed well with microcrystalline cellulose, and the mixture was prepared into granules; the granules were bagged to form 10000 bags. Wherein, the phillyrin/phillygeninin composition in the present example can be replaced with the composition of phillygeninin and phillyrin prepared in examples 5-29.

Example 54 Preparation of the Phillyrin/Phillygeninin Composition Capsules

The phillyrin/phillygeninin composition capsules were prepared according to the following mass ratio:

| | |
|---|---|
| phillyrin/phillygeninin composition (the weight ratio thereof was 94:6) | 2000 g |
| Spica *prunella* extract | 250 g |
| Herba *houttuyniae* extract | 500 g |
| Rhizoma *phragmites* extract | 250 g |
| starch | 1000 g |

According to the above ratio, the phillyrin/phillygeninin composition was mixed well with the above extract powder, and then mixed well with starch, and the mixture was prepared into capsules to form 10000 capsules. Wherein, the phillyrin/phillygeninin composition in the present example can be replaced with the composition of phillygeninin and phillyrin prepared in examples 5-29.

Test Example 1 Antiviral Test of the Formythin/Phillygeninin Composition

1 In Vitro Antiviral Test
1.1 Test Materials
(1) Drugs
① Phillyrin, white powder, produced by Dalian Fusheng Natural Drug Development Co. Ltd., the purity thereof was determined to be 99.5%, determined by HPLC equipped with both UV detector and evaporative light-scattering detector (ELSD) using area normalization method, and the content thereof was calibrated and confirmed to be 99.5% with phillyrin standard available from China Pharmaceutical and Biological Products for content determination.
② Phillygeninin, white powder and produced by Dalian Fusheng Natural Drug Development Co. Ltd., the purity thereof was determined to be 99.1%, determined by HPLC equipped with both UV detector and evaporative light-scattering detector (ELSD) using area normalization method, and the content thereof was calibrated and confirmed to be 99.1% with phillyrin standard available from China Pharmaceutical and Biological Products for content determination;
③ phillyrin/phillygeninin composition A, which was a white powder and produced by Dalian Fusheng Natural Drug Development Co. Ltd., was formed by two monomers of phillyrin and phillygeninin at a ratio; by calibrating using 99.5% phillyrin and 99.1% phillygeninin as the control, the contents of the each monomers in the phillyrin/phillygeninin composition was 98%; wherein the weight ratio of forsythin to phillygenol in the forsythin/phillygenol composition A was 98:2; phillyrin/phillygeninin composition B: which was a white powder and produced by Dalian Fusheng Natural Drug Development Co. Ltd., was formed by two monomers of phillyrin and phillygeninin; the weight ratio of phillyrin to phillygeninin in the phillyrin/phillygeninin composition A was 80:20.
④ Ribavirin injection, a colorless and transparent liquid, produced by He'nan Runhong Pharmaceutical Co. Ltd., lot number: 1206261, National medical Permit No: H19993553, 100 mg/ml, adopted as the positive control drug for the present test.
⑤ Oseltamivir phosphate, available from National Institute for Control of Pharmaceutical & Biological Products, with Lot number: 101096-200901, 100 mg/injection, adopted as the positive control drug for the present test.

The above-mentioned drugs were all dissolved with purified water, filtered, sterilized, sub-packaged, and stored at 4° C. for subsequent use; all of them were drugs to be tested in the present test.

(2) Cell Strain:
cell strain of Vero (African green monkey kidney cells) was preserved by College of Basic Medical Sciences of Jilin University.

(3) Virus Strains:
① influenza virus strains, parainfluenza virus strains, respiratory syncytial virus (RSV) strains: purchased from the Virus Institute of Chinese Preventive Medicine Academy of Science;
② Coxsackie virus $B_3$ ($CVB_3$) strains: was available from USA and preserved by our teaching and research office;
③ Coxsackievirus A16 (CoxA16) strains and enterovirus EV71 strains: were donated by Sendai National Hospital of Japan and preserved by the applicant Teaching and Research Office;
④ adenovirus (Adv) was available from the Pediatric Research Department of the First Hospital of Norman Bethune Medical University;
⑤ Herpes zoster simplex viruses type I (HSV-1) was purchased from the Institute for the Control of Pharmaceutical and Biological Products, Ministry of Health.

(4) Main Equipment and Reagents:
Biosafe cabinet: BHC-1300 II A/B3, AIRTECH;
$CO_2$ incubator: MCO-18AIC, SANYO;
inverted microscope: CKX41, OLYMPUS;
electronic analytical balance: AR1140/C, DHAUS;
culture medium: DMEM, HyClone;
fetal bovine serum: HyClone;
trypsin: Gibco;
MTT: Sigma;
DMSO: Tianjin Beilian Fine Chemicals Development Co., Ltd.

1.2 Test Method
(1) Preparation of Cells
Vero cells were subcultured for 1-2 days to form a film, and treated with the pancreatic enzyme when the boundary line was clear and the tri-dimensional sense and diopter were strong; when there were tip-like wells on the cell surface, the digestion was completed drained, and the cells were dispersed with several milliliters of culture medium, counted, and diluted to about $5 \times 10^7$ cells/L with the culture medium (DMEM containing 10% fetal bovine serum) and inoculated into a 96-well culture plate until the cells were grown into a monolayer.

(2) Determination of the Drug Toxicity
Cytotoxicity test: the drugs were diluted according to the concentrations shown in table 1-1 for determination of cytotoxicity.

TABLE 1-1

Drug Dilution Reference Table (unit: g/L)

| drug | gradient 1 | gradient 2 | gradient 3 | gradient 4 | gradient 5 | gradient 6 | gradient 7 | gradient 8 |
|---|---|---|---|---|---|---|---|---|
| phillyrin | 1 | 0.5 | 0.25 | 0.125 | 0.0625 | 0.03125 | 0.015625 | 0.078125 |
| Phillygeninin | 1 | 0.5 | 0.25 | 0.125 | 0.0625 | 0.03125 | 0.015625 | 0.078125 |
| phillyrin/phillygeninin composition A | 1 | 0.5 | 0.25 | 0.125 | 0.0625 | 0.03125 | 0.015625 | 0.078125 |
| phillyrin/phillygeninin composition B | 1 | 0.5 | 0.25 | 0.125 | 0.0625 | 0.03125 | 0.015625 | 0.078125 |
| Ribavirin | 5 | 2.5 | 1.25 | 0.625 | 0.3125 | 0.15625 | 0.078125 | 0.039063 |
| oseltamivir phosphate | 2 | 1 | 0.5 | 0.25 | 0.125 | 0.0625 | 0.03125 | 0.015625 |

The above drugs, which were diluted with a maintenance solution (DMEM containing 2% of fetal bovine serum) and had different concentrations, were added dropwise to the Vero monolayer cell, 0.2 ml for each well, the drugs were added in sextuplicate in 6 wells respectively. In addition, 6 wells were set up as normal control group (without drugs) while another 6 pores as blank control group (medium only). Cells were grown in a 37° C. incubator under 5% $CO_2$. CPE was observed with an inverted microscope and recorded every day. After 72 h, 20 μL MTT solution (5 mg·mL$^{-1}$) was added into each well to continue incubation for 4 h. The culture medium in each well was sucked and discarded, 100 μL DMSO was added to each well. Then the culture was shaken for 5 min, measured OD value at 492 nm to calculate the cell survival ratio. The cell survival ratio was analyzed using a Probit regression model in SPSS 18.0 statistical software, and the maximal nontoxic concentration ($TC_0$) and median toxic concentration ($TC_{50}$) of drugs against Vero cells were calculated.

(3) Determination of $TCID_{50}$ of Various Viruses

Various viruses were diluted by 10-fold decrements to have different dilutions of $10^{-1}$, $10^{-2}$, $10^{-3}$, $10^{-4}$, $10^{-5}$, and $10^{-6}$, and were sequentially inoculated onto a 96-well culture plate with monolayer Vero cells, 100 μL for each well, 6 wells for each dilution, and meanwhile, a normal cell control group was set up. It was incubated in 5% $CO_2$ at 37° C. for 2 h, the virus solution was discarded, thereupon 100 μL of cell maintenance solution was added to each well, and continued to incubate in 5% $CO_2$ at 37° C. The cytopathic results were observed under a microscope from the 3rd day on, and the results were determined and recorded on the 7th or 8th day, such that the highest dilution capable of causing positive lesion to occur in 50% of the cell wells was taken as the end point where positive lesion occurred in, and the virus titer was calculated by using a karber method.

$$\text{Formula } Log TCID_{50} = XM + \frac{1}{2}d - d\frac{\Sigma Pi}{100}$$

$TCID_{50}$: 50% histocyte infection dose;

XM: the logarithm of the highest concentration dilution of the virus;

d: the logarithm of the dilution coefficient (multiple);

Σpi: the sum of the each dilution lesion percentage.

(4) Impact of the Drug on the Virus-Induced Cytopathic Effects

A culture plate covered with monolayer cells was adopted, the culture medium was sucked and discarded, cells were inoculated at a virus attack amount corresponding to $100TCID_{50}$, absorbed in an incubator at 37° C. with 5% $CO_2$ for 2 h, various drug liquids with specific concentrations (about the maximal non-cytotoxic concentration or so) were added, and 6 wells were provided for culture for each concentration, 200 μL/well. Ribavirin injection and oseltamivir phosphate were provided as the positive drug control group, and a normal control group (neither virus nor drug was added) and a viral control group (a control group adding virus but no drug) were also provided, and the impact of the drug on the virus-induced CPE was observed. After 72 hours, the OD value was measured under 492 nm wavelength by using an MTT colorimetric method to calculate the antiviral effective rate (ER %) of the drugs. The analysis of variance (ANOVA) method in SPSS 18.0 statistical software was used to determine if there was a significant difference among different drugs groups on antiviral efficiency.

ER %=(the average OD value of the drug treated group–the average OD value of the virus control group)/(the average OD value of the cell control group–the average OD value of the virus control group)×100%

1.3 Test Results (3) $TCID_{50}$ of Each Virus $$Log TCID_{50} = -2 + 0.5 - \frac{100 + 100 + 50}{100} = -4 \quad \text{Parainfluenza virus}$$

$$Log TCID_{50} = -2 + 0.5 - \frac{100 + 100 + 50}{100} = -4 \quad \text{Influenza virus}$$

$$Log TCID_{50} = -2 + 0.5 - \frac{100 + 100 + 100 + 50}{100} = -5 \quad CVB_3$$

$$Log TCID_{50} = -2 + 0.5 - \frac{100 + 100 + 100 + 30}{100} = -4.8 \quad \text{HSV-1}$$

$$Log TCID_{50} = -2 + 0.5 - \frac{100 + 100 + 50}{100} = -4 \quad \text{AdV}$$

$$Log TCID_{50} = -2 + 0.5 - \frac{100 + 100 + 100 + 50}{100} = -5 \quad \text{RSV}$$

$$Log TCID_{50} = -2 + 0.5 - \frac{100 + 100 + 100 + 50}{100} = -5 \quad \text{CoxA16}$$

$$\text{Log}TCID_{50} = -2 + 0.5 - \frac{100 + 100 + 100 + 50}{100} = -5 \quad \text{EV71}$$

(2) Determination of the Drug Toxicity
1) Determination of the Cytotoxicity of Drugs The maximal non-toxic concentrations ($TC_0$) and median toxic concentrations ($TC_{50}$) of the various drugs on the Vero cell and concentrations for drugs used in antiviral test can be seen in Table 1-2.

As shown in the results of Table 1-3, the phillyrin/phillygeninin composition has significant inhibitory effects (P<0.01 or P<0.001) on all of the 8 viruses has an antiviral effective rate of 100% on the influenza virus, the parainfluenza virus, the Herpes zoster simplex viruses Type I (HSV-I), the enterovirus EV71 and the adenovirus (ADV), and has a significantly better therapeutic effect than phillyrin and phillygeninin. This indicates that the phillyrin/phillygeninin composition has a synergistic effect. Furthermore, the phillyrin/phillygeninin composition has a significantly better therapeutic effect on inhibition to influenza, the Coxsakie

TABLE 1-2

Results of Drug cytotoxicity test (unit: g/L)

| virus | phillyrin | Phillygeninin | phillyrin/ phillygeninin composition A | phillyrin/ phillygeninin composition B | Ribavirin | oseltamivir phosphate |
|---|---|---|---|---|---|---|
| maximal non-toxic concentration | 0.0066 | 0.011 | 0.010 | 0.0066 | 0.065 | 0.28 |
| half toxic concentration | 0.55 | 0.297 | 0.60 | 0.55 | 1.392 | 0.832 |
| | 0.30 | 0.01 | 0.02 | 0.01 | 0.01 | 0.70 | 0.30 |

2) Results of Protective Effects of Drugs on the Virus-Induced Cytopathy

The antiviral efficiency of the drugs on resistance to various viruses and the results of one-way analysis of variance using an ANOVA-method, were seen in Table 1-3 for details.

virus A16 (CoxA16), the respiratory syncytial virus (RSV), the herpes zoster simplex viruses type I (HSV-I), the adenovirus (ADV), the enterovirus EV71 and the coxsackie virus $B_3$(CVB$_3$) than the positive drug ribavirin (P<0.01 or P<0.001), and has a significantly better therapeutic effect on inhibition to influenza, the Coxsakie virus A16 (CoxA16),

TABLE 1-3

Statistical table of antiviral effective rate (ER %) of drugs

| virus | phillyrin | Phillygeninin | phillyrin/ phillygeninin composition A | phillyrin/ phillygeninin composition B | Ribavirin | oseltamivir phosphate |
|---|---|---|---|---|---|---|
| influenza virus | 75.38** | 75.35** | 100.00***#|▲▲▲▲●*###▲▲▲▲● | 97.60 | 57.49** | 81.76** |
| parainfluenza virus | 84.96** | 80.72** | 100.00***# | 99.51***#▲ | 91.56** | 94.52** |
| CoxA16 | 75.08** | 50.04 | 98.20***#| | 97.63 | 0.70 | 2.95 |
| RSV | 80.40** | 80.88** | 96.22****# | 95.88 | 50.08* | 37.60 |
| HSV-I | 85.00** | 84.30** | 100.00***#▲▲●● | 99.24.00***#▲▲●● | 62.92** | 66.56** |
| ADV | 75.14** | 50.61 | 100.00***# | 94.10 | 0.43 | 10.31 |
| EV71 | 84.85** | 75.86** | 100.00***# | ***#▲▲▲▲●●● | 4.25 | 51.86 |
| CVB$_3$ | 75.27** | 50.89 | 92.67***#| | 90.49 | 13.44 | 1.64 |

Note:
compared with the virus control group,
*P < 0.05,
**P < 0.01;
when the phillyrin/phillygeninin composition was compared with phillyrin,
P < 0.05,
P < 0.01;
when the phillyrin/phillygeninin composition was compared with phillygeninin,
▲P < 0.05,
▲▲P < 0.01;
when the phillyrin/phillygeninin composition was compared with ribavirin,
△P < 0.05,
△△P < 0.01,
△△△P < 0.001;
when the phillyrin/phillygeninin composition was compared with oseltamivir phosphate,
●P < 0.05,
●●P < 0.01,
●●●P < 0.001.

the respiratory syncytial virus (RSV), the herpes zoster simplex viruses type I (HSV-I), the adenovirus (ADV), the enterovirus EV71 and the coxsackie virus B3 (CVB3) than oseltamivir phosphate ($P<0.05$, or $P<0.01$, $P<0.001$).

2. In Vivo Antiviral Test 2.1 Test Materials (1) Test Animals

Kunming mice, Medicinal Animal No. 10-5219, were provided by Experimental Animal Center of Norman Bethune Health Science Center of Jilin University.

(2) Experimental Instruments and Reagents

| Instrument Name | Model | Manufacturer |
| --- | --- | --- |
| Quantitative PCR Instrument | 7300 | ABI |
| PCR Instrument | ES-60J | Shenyang Longteng Electronic Weighing Instrument Co., Ltd. |
| Electronic Analytical Balance | FA1004 | Shenyang Longteng Co., Ltd. |
| CO2 Incubator | HG303-5 | Nanjing Experimental Instrument Factory |
| Superclean Bench | SW-CJ-IF | Suzhou Antai Technology Co., Ltd. |
| Inverted Microscope | CKX41 | Olympus Instrument |
| −80° C. ultra low temperature freezer | TECON-5082 | Australia |
| Water bath oscillator | HZS-H | Haerbin Donglian Co., Ltd. |
| Microplate reader | TECAN A-5082 | Australia |
| Spectrophotometer | Model 7550 | Japan |

2.2 Test Method (1) Determination of the Median Lethal Dose of the Mice Due to Influenza Virus and Parainfluenza Virus The influenza virus and the parainfluenza virus (cell lysate) were diluted by a 10-fold decrement into virus liquids with concentrations of $10^{-1}$, $10^{-2}$, $10^{-13}$ $10^{-4}$, and $10^{-5}$. 120 Kunming mice were obtained, 60 of which were provided for the influenza virus group and the remaining 60 were provided for the parainfluenza virus group; the 60 mice were randomly divided into 6 groups separately; the mice were lightly anesthetized with ether, and were infected with virus liquids having different dilutions at 0.03 mL/mouse by means of nasal dripping. Meanwhile blank control group was set, and the virus suspension was replaced with saline. Death and survival were regarded as the observational indexes, and observation was performed every day until 14 days after infection. Those mices died within 24 hours after infection were nonspecific death and not counted up, and the virus liquid LD50 was calculated by using the Karber method. The calculation formula is:

$$\text{Log}LD_{50} = XM + \frac{1}{2}d - d\frac{\Sigma Pi}{100}$$

[wherein: $LD_{50}$: median lethal dose; XM: the logarithm of the highest concentration dilution of virus; d: the logarithm of the dilution coefficient (multiple); $\Sigma pi$: the sum of the each dilution lesion percentage].

(2) Research on Resistance of the Phillyrin/Phillygeninin Composition to Pneumonia Caused by Anti-Influenza Virus and Parainfluenza Virus Infection.

1) Test Animals and Groups 540 four weeks old Kunming mice were adopted to perform two tests.

First, 270 mice were adopted and randomly divided into 27 groups (10 mice for each group) for the test of determining lung index of the mice infected by the influenza virus and parainfluenza virus and lung index inhibition rate of the phillyrin/phillygeninin composition; 90 mice were adopted for each test, and the test was repeated for 3 times. Additional 270 mice were adopted and randomly divided into 27 groups (10 mice for each group) for the test of determining lung suspension virus hemagglutination titer of the composition of phillyrin and phillygeninin; 90 mice were adopted for each test, and the test was repeated for 3 times.

2) Infection Method

Degreasing cotton was placed in a 200-300 mL beaker, and then a suitable amount of ether (just for making the cotton wet) was poured therein, the beaker containing the degreasing cotton was inverted upside down, the mice were put therein for anesthetization; when the mice were extremely excited and obviously weak, the mice were made to lie on their backs and infected with $15LD_{50}$ influenza virus and parainfluenza virus by means of nasal dripping at 0.03 ml/nostril; and the virus suspension was replaced with saline in the normal control group.

3) Administration Method and Administration Dosage

The phillyrin/phillygeninin composition group A, the phillyrin/phillygeninin composition group B, the phillygeninin group, the phillyrin group, the ribavirin control group and the oseltamivir phophate control group are separately taken for conventional intragastric administration one day before infection; the phillyrin/phillygeninin composition groups A and B were high, medium and low dose groups respectively, and the administration doses were 13.0, 6.5, and 3.25 mg/kg respectively; the administration dose of the phillyrin group was 13 mg/kg, the administration dose of the phillygeninin group was 13 mg/kg, the administration dose of the ribavirin positive drug group was 58.5 mg/kg, the administration dose of the oseltamivir phosphate group was 19.5 mg/kg, the administration was performed once a day for 5 consecutive days, and perfusion of normal saline of the same volume is performed for the normal control group and the virus control group.

4) Observational Index

① Lung Index Determination

On the fifth day after drugs were administered to the mice, first the mice were prohibited from drinking water for 8 hours; then, after the mice were weighed, their eyes were removed and the animals were sacrificed by exsanguination through eye enucleation. Then the lungs were removed after the opening of the chest, washed twice with normal saline followed by removal of the moisture from surface with a filter paper and weighed by using an electronic balance. Lung index and the inhibitory rate of the lung index were calculated according to the following equations:

Lung index=(mice lung weight/mice body weight)× 100%;

Inhibitory rate of the lung index=(average lung index of the infection model group−average lung index of the test group)/average lung index of the infection model group×100%.

② Determination of Lung Suspension Virus Hemagglutination Titer

Various groups of mice lungs were respectively taken on the fifth day after treatment, and were ground into homogenate by a homogenizer at a low temperature; the homogenate was diluted into 10% of lung tissue suspension with normal saline; centrifugation was performed to obtain a supernatant, which was double diluted and dripped to a titration plate with 0.2 ml/well; 0.2 ml of 1% chicken erythrocyte suspension was added into each well and mixed uniformly; the titration plate was placed in a room temperature environment for 30 minutes to observe and record hemagglutination titers. The end point appears when the erythrocyte was agglutinated to be (++), and its titer was expressed by the suspension dilution multiple.

2.3 Test Results and Analysis (1) Determination Result of the Median Lethal Dose of the Mice Due to the Influenza Virus and the Parainfluenza Virus Kunming mice in the test groups were respectively infected nasally with 30 μL of influenza virus and parainfluenza virus liquids of different concentrations; on the third day of infection, all of the mice in the first three groups ($10^{-1}$ group, $10^{-2}$ group and $10^{-3}$ group based on virus concentrations) experienced disease symptoms of different degrees: pilomotor fur, trembling, degreased appetite and so on; on the fifth day, the mice stumble; on the sixth day, the mice in the group of the highest virus concentration began to die, and death occurred successively in the remaining groups on the seventh day after infection. After the observation of 14 days was complete, the mortality of the mice of each group was counted, and the result can be seen in Tables 1-4 and 1-5. By calculation, $LD_{50}$ of the influenza virus was a dilution of $10^{-2.9}$, and $LD_{50}$ of the parainfluenza virus was a dilution of $10^{-2.5}$.

TABLE 1-4

Statistics of test results of median lethal dose of the influenza virus

| Influenza virus group | Cumulative mortality | Cumulative survival | Cumulative mortality rate |
|---|---|---|---|
| 10-1 group | 9 | 1 | 90% |
| 10-2 group | 7 | 3 | 70% |
| 10-3 group | 4 | 6 | 40% |
| 10-4 group | 3 | 7 | 30% |
| 10-5 group | 1 | 9 | 10% |
| Blank group | 0 | 10 | 0% |

$LD_{50}$ of the virus was calculated by using a Karber method. Log $LD_{50}$ of the influenza virus was as follows:

$$LogLD_{50} = XM + \frac{1}{2}d - d\frac{\Sigma Pi}{100} =$$
$$-1 + 0.5 - (80\% + 60\% + 40\% + 20\% + 0\% + 0\%) = -2.9$$

TABLE 1-5

Statistics of test results of median lethal dose of the parainfluenza virus

| Parainfluenza virus group | Cumulative mortality | Cumulative survival | Cumulative mortality rate |
|---|---|---|---|
| 10-1 group | 8 | 2 | 80% |
| 10-2 group | 6 | 4 | 60% |
| 10-3 group | 4 | 6 | 40% |
| 10-4 group | 2 | 8 | 20% |
| 10-5 group | 0 | 10 | 0% |
| Blank group | 0 | 10 | 0% |

$LD_{50}$ of the virus was calculated by using the Karber method. Log $LD_{50}$ of the parainfluenza virus was as follows:

$$LogLD_{50} = XM + \frac{1}{2}d - d\frac{\Sigma Pi}{100} =$$
$$-1 + 0.5 - (90\% + 70\% + 40\% + 30\% + 10\% + 0\%) = -2.5$$

(2) Results of Effects of the Phillyrin/Phillygeninin Composition on Resistance to Pneumonia Caused by the Influenza Virus and Parainfluenza Virus Infections.

① Lung Index Determination

After the mice were infected with the influenza virus and the parainfluenza virus, the average lung index result showed that: compared with the infection model group, the lung indexes of the normal control group, the phillyrin group (13.0 mg/kg/d), the phillygeninin group (16.0 mg/kg/d), the three dose groups of the phillyrin/phillygeninin compositions A and B (low-dose group 3.25 mg/kg/d, medium-dose group 6.5 mg/kg/d, high-dose group 13.0 mg/kd/d), the ribavirin group, and the oseltamivir phosphate group decrease significantly (P<0.05 or P<0.01), wherein the phillyrin/phillygeninin composition has significant protective effect within the concentration range of 3.25-13.0 mg/kg/d, significantly decrease all the lung indexes, and has a significantly better therapeutic effect on the inhibition rate to the lung tissue lesion index than the phillyrin group and the phillygeninin group (P<0.01 or P<0.05). See Tables 1-6 and 1-7 for the results.

TABLE 1-6

The inhibition rate of the phillyrin/phillygeninin composition to the lung index of the influenza virus infected mice (n = 3)

| Groups | | Drug dose (mg/kg/d) | Lung index ($\bar{x}$ (S)) | Lung index inhibition rate | P value | P value |
|---|---|---|---|---|---|---|
| Normal control group | | 0 | 1.274 ± 0.102 | — | | |
| Virus control group | | 0 | 1.488 ± 0.084 | — | | |
| Ribavirin group | | 58.5 | 1.281 ± 0.061 | 13.90 | *<0.05 | |
| Oseltamivir phosphate group | | 19.5 | 1.178 ± 0.066 | 19.84 | **<0.01 | |
| Phillyrin group | | 13.0 | 1.280 ± 0.040 | 14.00 | *<0.05 | |
| Phillygeninin group | | 13.0 | 1.302 ± 0.046 | 12.51 | *<0.05 | |
| Phillyrin/ | High dose group | 13.0 | 1.049 ± 0.056 | 29.52 | **<0.01 | ##▲▲<0.01 |
| phillygeninin | Medium dose group | 6.5 | 1.129 ± 0.041 | 24.15 | **<0.01 | ▲#<0.05 |
| composition A | Low dose group | 3.25 | 1.184 ± 0.039 | 20.40 | **<0.01 | ▲#<0.05 |
| Phillyrin/ | High dose group | 13.0 | 1.070 ± 0.056 | 28.10 | **<0.01 | ##▲▲<0.01 |

TABLE 1-6-continued

The inhibition rate of the phillyrin/phillygeninin composition to the lung index of the influenza virus infected mice (n = 3)

| | Groups | Drug dose (mg/kg/d) | Lung index ($\bar{x}$ (S)) | Lung index inhibition rate | P value | P value |
|---|---|---|---|---|---|---|
| phillygeninin composition B | Medium dose group | 6.5 | 1.131 ± 0.041 | 24.00 | **<0.01 | ▲#<0.05 |
| | Low dose group | 3.25 | 1.197 ± 0.039 | 19.56 | **<0.01 | ▲#<0.05 |

When each test group is compared with the virus control group, *P<0.5, **P<0.01; when the phillyrin/phillygeninin composition is compared with the phillyrin, #P<0.05, ##P<0.01; when the phillyrin/phillygeninin composition is compared with the phillygeninin, ▲P<0.05, ▲▲P<0.01.

TABLE 1-7

The inhibition rate of the phillyrin/phillygeninin composition to the lung index of the parainfluenza virus infected mice (n = 3)

| | Groups | Drug dose (mg/kg/d) | Lung index ($\bar{x}$ (S)) | Lung index Inhibition rate | P value | P value |
|---|---|---|---|---|---|---|
| Normal control group | | 0 | 1.305 ± 0.031 | — | | |
| Virus control group | | 0 | 1.591 ± 0.062 | — | | |
| Ribavirin group | | 58.5 | 1.340 ± 0.065 | 15.76 | *<0.05 | |
| Oseltamivir phosphate group | | 19.5 | 1.243 ± 0.054 | 21.85 | *<0.01 | |
| Phillyrin group | | 13.0 | 1.335 ± 0.062 | 16.10 | *<0.01 | |
| Phillygeninin group | | 13.0 | 1.357 ± 0.050 | 14.69 | *<0.01 | |
| Phillyrin/ phillygeninin composition A | High dose group | 13.0 | 1.068 ± 0.058 | 32.87 | *<0.01 | ##▲▲<0.01 |
| | Medium dose group | 6.5 | 1.143 ± 0.065 | 28.13 | *<0.01 | #▲▲<0.05 |
| | Low dose group | 3.25 | 1.177 ± 0.044 | 26.01 | *<0.01 | #▲<0.05 |
| Phillyrin/ phillygeninin composition B | High dose group | 13.0 | 1.101 ± 0.058 | 30.79 | *<0.01 | ##▲▲<0.01 |
| | Medium dose group | 6.5 | 1.158 ± 0.065 | 27.22 | *<0.01 | #▲▲<0.05 |
| | Low dose group | 3.25 | 1.188 ± 0.044 | 25.30 | *<0.01 | #▲<0.05 |

When each test group is compared with the virus control group, *P<0.05, P<0.01; when the phillyrin/phillygeninin composition is compared with the phillyrin, #P<0.05, ##P<0.01; when the phillyrin/phillygeninin composition is compared with the phillygeninin, ▲P<0.05.

② Determination of Lung Suspension Virus Hemagglutination Titer

After the mice were infected with the influenza virus and the parainfluenza virus, the lung tissue hemagglutination titers (InX) of the infection model groups were 32.40 and 33.11 respectively; after treatment with the phillyrin/phillygeninin compositions A and B of different concentrations for 5 days, the lung tissue virus hemagglutination titers both decreased to some extent, and compared with the infection model groups, the difference was significant (P<0.01), and their different dose groups of the phillyrin/phillygeninin compositions A and B have significantly lower influenza and parainfluenza virus hemagglutination titers than the phillyrin group and the phillygeninin group (P<0.05-P<0.001). This indicates that the phillyrin/phillygeninin composition has the synergistic effect, and has a significantly higher inhibition rate to the virus proliferation than the phillyrin group and the phillygeninin group (P<0.05-P<0.001), wherein, the high, medium and low dose groups of the phillyrin/phillygeninin compositions A and B have significantly higher inhibition rate to the lung suspension hemagglutination titer of the influenza virus infected mice than the phillyrin group and the phillygeninin group (P<0.01-P<0.001). See Tables 1-8 and 1-9 for the details of the above test results.

TABLE 1-8

Impact of the phillyrin/phillygeninin composition on the lung suspension hemagglutination titer of the influenza virus infected mice (n = 3)

| | Groups | Drug dose (mg/kg/d) | Hemagglutination titer (InX) | Inhibition rate (%) | P value | P value |
|---|---|---|---|---|---|---|
| Normal control group | | 0 | 0 | | | |
| Virus control group | | 0 | 32.40 ± 1.105 | | | |
| Ribavirin group | | 58.5 | 21.91 ± 1.050 | 32.39 | *<0.01 | |
| Oseltamivir phosphate group | | 19.5 | 20.50 ± 1.123 | 36.73 | *<0.01 | |
| Phillyrin Group | | 13.0 | 22.06 ± 1.120 | 31.90 | *<0.01 | |
| Phillygeninin group | | 13.0 | 22.61 ± 1.059 | 30.22 | *<0.01 | |
| Phillyrin/ phillygeninin composition A | High dose group | 13.0 | 17.70 ± 0.618 | 45.36 | *<0.01 | ###▲▲▲<0.001 |
| | Medium dose group | 6.5 | 19.21 ± 0.450 | 40.72 | *<0.01 | ##▲▲<0.01 |
| | Low dose group | 3.25 | 20.71 ± 1.439 | 36.08 | *<0.01 | #▲<0.05 |

TABLE 1-8-continued

Impact of the phillyrin/phillygeninin composition on the lung suspension hemagglutination titer of the influenza virus infected mice (n = 3)

| Groups | | Drug dose (mg/kg/d) | Hemagglutination titer (InX) | Inhibition rate (%) | P value | P value |
|---|---|---|---|---|---|---|
| Phillyrin/ | High dose group | 13.0 | 17.70 ± 0.618 | 45.36 | *<0.01 | ###▲▲▲<0.001 |
| phillygeninin | Medium dose group | 6.5 | 19.21 ± 0.450 | 40.72 | *<0.01 | ##▲▲▲<0.01 |
| composition B | Low dose group | 3.25 | 20.71 ± 1.439 | 36.08 | *<0.01 | #▲<0.05 |

TABLE 1-9

Impact of the phillyrin/phillygeninin compositions on the lung suspension hemagglutination titers of the parainfluenza virus infected mice (n = 3)

| Groups | | Drug dose (mg/kg/d) | Hemagglutination titer (InX) | Inhibition rate (%) | P value | P value |
|---|---|---|---|---|---|---|
| Normal control group | | 0 | 0 | | | |
| Virus control group | | 0 | 33.11(1.210 | | | |
| Ribavirin group | | 58.5 | 23.22(1.091 | 29.86 | *<0.05 | |
| Oseltamivir phosphate group | | 19.5 | 22.05(1.055 | 33.40 | *<0.01 | #<0.05 |
| Phillyrin Group | | 13.0 | 23.17(1.059 | 30.01 | *<0.01 | #<0.05 |
| Phillygeninin group | | 13.0 | 23.79(1.072 | 28.15 | *<0.01 | #>0.05 |
| Phillyrin/ | High dose group | 13.0 | 17.38(0.955 | 47.50 | *<0.01 | ###▲▲▲<0.001 |
| phillygeninin | Medium dose group | 6.5 | 19.04(0.501 | 42.49 | *<0.01 | ##▲▲▲<0.01 |
| composition A | Low dose group | 3.25 | 20.36(0.824 | 38.52 | *<0.01 | ##▲▲<0.01 |
| Phillyrin/ | High dose group | 13.0 | 17.97(0.955 | 45.73 | *<0.01 | ###▲▲▲<0.001 |
| phillygeninin | Medium dose group | 6.5 | 19.69(0.501 | 40.52 | *<0.01 | ##▲▲▲<0.01 |
| composition B | Low dose group | 3.25 | 20.81(0.824 | 37.15 | *<0.01 | ##▲▲▲<0.01 |

In Tables 1-8 and 1-9, when each test group was compared with the viral control group, *P<0.05, **P<0.01; when the phillyrin/phillygeninin composition group was compared with the phillyrin, #P<0.05, ##P<0.01, ###P<0.001; when the phillyrin/phillygeninin composition group was compared with the phillygeninin, ▲P<0.05, ▲▲P<0.01, ▲▲▲P<0.001.

Example 2 Antipyretic and Anti-Inflammatory Tests of the Phillyrin/and Phillygeninin Composition 1.1 Test Materials (1) Test Animals: Wistar rats, weight: 120~250 g, male and femal combination, Medicinal Animal No. 13-1225; Japanese white rabbits, male, body weight: 1.5~2.0 kg, Medicinal Animal No. 10-5115. Both the rats and the rabbits were provided by Changchun Gaoxin Medical Animal Experiment Center, and animal feeds were provided by Center for Experimental Animals of Jilin University.

(2) Test Drugs

① Phillyrin, white powder, manufactured by Dalian Fusheng Natural Drug Development Co. Ltd., had a purity of 99.5%, which was determined by HPLC equipped with both UV detector and evaporative light-scattering detector (ELSD) using area normalization method, and the content thereof was calibrated and confirmed to be 99.5% with the phillyrin standard control from China Pharmaceutical and Biological Products for content determination.

② Phillygeninin, a white powder, manufactured by Dalian Fusheng Natural Drug Development Co. Ltd., the purity thereof was determined to be 99.1%, determined by HPLC equipped with both UV detector and evaporative light-scattering detector (ELSD) using area normalization method;

③ Phillyrin/phillygeninin composition, which was a white powder and manufactured by Dalian Fusheng Natural Drug Development Co. Ltd., was formed by two monomers of phillyrin and phillygeninin at a ratio; by calibrating using 99.5% phillyrin and 99.1% phillygeninin as the control, the contents of the two monomers in the phillyrin/phillygeninin composition were both 98%; wherein the weight ratio of forsythin to phillygenol in the forsythin/phillygenol composition A was 98:2; the weight ratio of phillyrin to phillygeninin in the phillyrin/phillygeninin composition B was 80:20.

1.2 Main Instruments and Reagents

YLS-7A rat paw swelling measurement instrument (Equipment Station in Shandong Academy of Medical Sciences);

722 spectrophotometer (manufactured by Shanghai Spectrum Instruments Ltd.);

Portable Digital Temperature Measuring Instrument (model WSC-411P, the Third Company of Shanghai Pudong);

Pilocarpine (Tianjin People Pharmaceutical Factory, Batch No. 0130112);

Histamine (Institute of Biochemistry and Cell Biology, SIBS, CAS, Batch No. 0130115);

5-hydroxytryptamine (Institute of Biochemistry and Cell Biology, SIBS, CAS, Batch No. 0130623);

Evans blue (Shanghai Chemical Reagents Purchases-supply Station, Batch No. 0130217);

Chlorpheniramine maleate tablets (Changchun Economic Development Zone Pharmaceutical Co., Ltd., Batch No. 0130801);

Carrageenin (Medical Institute of Pharmacology in Jilin, Batch No. 0130502);

Paracetamol tablets (Liaoyuan City Baikang Pharmaceutical Co., Ltd., Batch No. 0130512);

Aspirin tablets (Baicheng Wanda Pharmaceutical Co., Ltd., Batch No. 0130305);

*Saccharomyces cerevisiae* (Beijing AOBOXING Bio-tech Co., Ltd., Batch No. 013020);

Typhoid and paratyphoid vaccine (Changchun Institute of Biological Products Co., Ltd., Batch No. 0130216).

1.3 Statistical Treatment

Rank sum test, $X^2$ test and t test for comparison of two samples were used in statistical analysis.

2.1 Test of Effects of the Phillyrin/Phillygeninin Composition on Sweat Secretion of Rat Paws (Coloring Method)

(1) Materials and Methods

The test is based on a mechanism that distribution of sweat glands is present in footpads of rat paws, the amount of sweat secretion and variation thereof can be observed by using a mechanism that a purple color can be produced by contacting iodine and starch when encountered with sweat.

500 Wistar rats with equal male and female number were used, weighing of 120~150 g. These rats were randomly divided into 50 groups by weight and gender, i.e., namely 5 groups for the control groups (0.5% methyl cellulose), 5 groups for phillyrin groups, 5 groups for phillygeninin groups, 5 groups for the low, medium and high dose groups (2.5, 5, 10 mg/kg, respectively) of phillyrin/phillygeninin compositions A and B respectively, and 5 groups for the positive drug pilocarpine groups (35 mg/kg). Each group has 10 rats, 10 groups of rates are used for each test, which has 5 time periods (1, 5, 10, 15 and 20 min). The rats were placed into a self-made rat fixation bag, and both hind limbs of the rats were exposed. Dirt on the right paws was gently cleaned away using cotton swabs containing anhydrous alcohol. Pilocarpine solution was administered by subcutaneous injection, the remaining groups were subjected to intragastric administration. At 1 h (30 min for the pilocarpine group) after administration, pre-existing sweat and sweat generated due to struggle on the right paw of each rat in each group was gently wiped away with dry cotton swabs, then the paws were coated with solution A (dissolving 2 g iodine in 100 ml anhydrous alcohol) of Hetian-gaoyuanshi's reagent. After complete dryness, the paws were thinly coated with solution B (uniform mixture of 50 g soluble starch and 100 ml castor oil) of Hetian-gaoyuanshi's reagent. The color and number of dark purple coloring spots (i.e. sweat spots) were carefully observed at 1, 5, 10, 15 and 20 min after the coating of the solution B respectively with magnifying glass. After the test was completed, statistical treatment was performed according to the rank sum test with two-sample comparison, thereby comparing the differences among the various groups.

(2) Results

Compared with the control group, the medium and high dose groups (5, 10 mg/kg) of the phillyrin/phillygeninin compositions both have significant promoting effects on the sweat secretion of the rat paws at 10, 15 and 20 min after the coating of solution B ($p<0.05$), and the 2.5 mg/kg group of the phillyrin/phillygeninin compositions has a significant promoting effect on the sweat secretion of the rat paws at 15 and 20 min after the coating of solution B ($p<0.05$). Their sudorific functions were approximately equivalent to that of the positive drug pilocarpine, and these groups had characteristics of slowly promoting the sweat secretion of the rat paws. The high dose group of the phillyrin/phillygeninin composition has a significantly better prompting effect on the sweat secretion of the rat paws at 10, 15 and 20 min after the coating of solution B than the phillyrin and the phillygeninin ($p<0.05$). The medium dose group of the phillyrin/phillygeninin composition has a significantly better prompting effect on the sweat secretion of the rat paws at 10 and 15 min after the coating of solution B than the phillyrin and the phillygeninin ($p<0.05$). The low dose group of phillyrin/phillygeninin composition has a significantly better prompting effect on the sweat secretion of the rat paws at 15 min after the coating of solution B than the phillyrin and the phillygeninin ($p<0.05$). The above results showed that the phillyrin/phillygeninin composition has a significantly better effect on promotion of the sweat secretion of rat paws than the phillyrin and the phillygeninin. See Tables 2-1, 2-2, 2-3, 2-4 and 2-5 for details.

TABLE 2-1

Effects of the phillyrin/phillygeninin composition on the sweat secretion of paws of normal rats (coloring method)

| Groups | Animal number | Animal number of sweat spots of each level after coating solution B for 1 minute (rats) | | | | | P value |
|---|---|---|---|---|---|---|---|
| | | − | + | ++ | +++ | ++++ | |
| Control group | 10 | 2 | 2 | 3 | 2 | 1 | |
| Phillyrin | 10 | 0 | 2 | 2 | 2 | 4 | >0.05 |
| Phillygeninin | 10 | 0 | 1 | 3 | 3 | 3 | >0.05 |
| Pilocarpine 35.0 mg/kg | 10 | 0 | 1 | 3 | 1 | 5 | >0.05 |
| Phillyrin/phillygeninin composition A | | | | | | | |
| 2.5 mg/kg | 10 | 0 | 2 | 2 | 1 | 5 | >0.05 |
| 5.0 mg/kg | 10 | 0 | 2 | 2 | 1 | 5 | >0.05 |
| 10.0 mg/kg | 10 | 0 | 2 | 2 | 1 | 5 | >0.05 |
| Phillyrin/phillygeninin composition B | | | | | | | |
| 2.5 mg/kg | 10 | 0 | 3 | 2 | 0 | 5 | >0.05 |
| 5.0 mg/kg | 10 | 0 | 3 | 1 | 1 | 5 | >0.05 |
| 10.0 mg/kg | 10 | 0 | 3 | 1 | 1 | 5 | >0.05 |

TABLE 2-2

Effects of the phillyrin/phillygeninin composition on the
sweat secretion of the paws of nomal rats (coloring method)

| Groups | Animal number | Animal number of sweat spots of each level after coating solution B for 5 minute (rats) | | | | | P value |
|---|---|---|---|---|---|---|---|
| | | − | + | ++ | +++ | ++++ | |
| Control group | 10 | 0 | 4 | 1 | 4 | 1 | |
| Phillyrin | 10 | 0 | 1 | 2 | 2 | 5 | >0.05 |
| Phillygeninin | 10 | 0 | 1 | 3 | 2 | 4 | >0.05 |
| Pilocarpine 35.0 mg/kg | 10 | 0 | 1 | 2 | 1 | 6 | <0.05* |
| Phillyrin/phillygeninincomposition A | | | | | | | |
| 2.5 mg/kg | 10 | 0 | 0 | 1 | 4 | 5 | >0.05 |
| 5.0 mg/kg | 10 | 0 | 1 | 1 | 3 | 5 | >0.05 |
| 10.0 mg/kg | 10 | 0 | 1 | 3 | 2 | 5 | >0.05 |
| Phillyrin/phillygeninincompositionB | | | | | | | |
| 2.5 mg/kg | 10 | 0 | 2 | 2 | 1 | 5 | >0.05 |
| 5.0 mg/kg | 10 | 0 | 1 | 2 | 2 | 5 | >0.05 |
| 10.0 mg/kg | 10 | 0 | 1 | 3 | 1 | 5 | >0.05 |

TABLE 2-3

Effects of the phillyrin/phillygeninin composition on the
sweat secretion of the paws of nomal rats (coloring method)

| Groups | Animal number | Animal number of sweat spots of each level after coating solution B for 10 minute (rats) | | | | | P value |
|---|---|---|---|---|---|---|---|
| | | − | + | ++ | +++ | ++++ | |
| Control group | 10 | 0 | 3 | 2 | 4 | 1 | |
| Phillyrin | 10 | 0 | 1 | 1 | 3 | 5 | >0.05 |
| Phillygeninin | 10 | 0 | 1 | 3 | 1 | 5 | >0.05 |
| Pilocarpine 35.0 mg/kg | 10 | 0 | 0 | 2 | 1 | 6 | <0.05* |
| Phillyrin/phillygeninincomposition A | | | | | | | |
| 2.5 mg/kg | 10 | 0 | 0 | 1 | 4 | 5 | >0.05 |
| 5.0 mg/kg | 10 | 0 | 2 | 1 | 1 | 6 | <0.05*#▲ |
| 10.0 mg/kg | 10 | 0 | 1 | 2 | 4 | 6 | <0.05*#▲ |
| Phillyrin/phillygeninincompositionB | | | | | | | |
| 2.5 mg/kg | 10 | 0 | 0 | 2 | 3 | 5 | >0.05 |
| 5.0 mg/kg | 10 | 0 | 3 | 0 | 1 | 6 | <0.05*#▲ |
| 10.0 mg/kg | 10 | 0 | 1 | 1 | 1 | 6 | <0.05*#▲ |

TABLE 2-4

Effects of the phillyrin/phillygeninin composition on the
sweat secretion of the paws of nomal rats (coloring method)

| Groups | Animal number | Animal number of sweat spots of each level after coating solution B for 15 minute (rats) | | | | | P value |
|---|---|---|---|---|---|---|---|
| | | − | + | ++ | +++ | ++++ | |
| Control group | 10 | 0 | 3 | 2 | 4 | 1 | |
| Phillyrin | 10 | 0 | 1 | 2 | 4 | 5 | <0.05* |
| Phillygeninin | 10 | 0 | 1 | 1 | 3 | 5 | >0.05 |
| Pilocarpine 35.0 mg/kg | 10 | 0 | 0 | 2 | 1 | 6 | <0.05* |

TABLE 2-4-continued

Effects of the phillyrin/phillygeninin composition on the sweat secretion of the paws of nomal rats (coloring method)

| Groups | Animal number | Animal number of sweat spots of each level after coating solution B for 15 minute (rats) | | | | | P value |
|---|---|---|---|---|---|---|---|
| | | − | + | ++ | +++ | ++++ | |
| Phillyrin/phillygenininComposition A | | | | | | | |
| 2.5 mg/kg | 10 | 0 | 2 | 1 | 1 | 6 | <0.05*▲ |
| 5.0 mg/kg | 10 | 0 | 1 | 2 | 1 | 6 | <0.05*▲ |
| 10.0 mg/kg | 10 | 0 | 0 | 3 | 1 | 6 | <0.05*#▲ |
| Phillyrin/phillygenininCompositionB | | | | | | | |
| 2.5 mg/kg | 10 | 0 | 3 | 0 | 1 | 6 | <0.05*▲ |
| 5.0 mg/kg | 10 | 0 | 2 | 1 | 1 | 6 | <0.05*▲ |
| 10.0 mg/kg | 10 | 0 | 1 | 2 | 1 | 6 | <0.05*#▲ |

TABLE 2-5

Effects of the phillyrin/phillygeninin composition on the sweat secretion of the paws of nomal rats (coloring method)

| Groups | Animal number | Animal number of sweat spots of each level after coating solution B for 20 minute (rats) | | | | | P value |
|---|---|---|---|---|---|---|---|
| | | − | + | ++ | +++ | ++++ | |
| Control group | 10 | 0 | 3 | 2 | 4 | 1 | |
| Phillyrin | 10 | 0 | 0 | 4 | 0 | 6 | <0.05* |
| Phillygeninin | 10 | 0 | 0 | 1 | 4 | 5 | <0.05* |
| Pilocarpine 35.0 mg/kg | 10 | 0 | 0 | 2 | 1 | 6 | <0.05* |
| Phillyrin/phillygenininComposition A | | | | | | | |
| 2.5 mg/kg | 10 | 0 | 1 | 2 | 1 | 6 | <0.05* |
| 5.0 mg/kg | 10 | 0 | 0 | 3 | 1 | 6 | <0.05* |
| 10.0 mg/kg | 10 | 0 | 0 | 2 | 2 | 6 | <0.05*#▲ |
| Phillyrin/phillygenininCompositionB | | | | | | | |
| 2.5 mg/kg | 10 | 0 | 2 | 1 | 1 | 6 | <0.05* |
| 5.0 mg/kg | 10 | 0 | 1 | 2 | 1 | 6 | <0.05* |
| 10.0 mg/kg | 10 | 0 | 0 | 2 | 2 | 6 | <0.05*#▲ |

Evaluation Standards for Sweat Spot Levels:
"−" no sweat spot on rat paw pad surface;
"+" sweat spot occasionally observed on rat paw pad surface, with sweat area of below about 10% of the paw surface;
"++" sweat spot dispersed on rat paw pad surface, with sweat area of about 11-40% of the paw surface;
"+++" sweat spot dispersed on rat paw pad surface, with sweat area of about 41-70% of the paw surface;
"++++" sweat spot evenly distributed on rat paw pad surface, with sweat area of over 71% of the paw surface.

Comparison between each test group and the viral control group, *P<0.05; comparison between phillyrin/phillygeninin composition with phillyrin, #P<0.05. Comparison between phillyrin/phillygeninin composition with phillygeninin, ▲P<0.05.

2.2 Effects of the Phillyrin/Phillygeninin Composition on the Sweat Secretion of the Rat Paws (Histomorphological Observation Method)
(1) Materials and Methods This test is based on a mechanism that when a rat is in an excited state, in addition to the increase of sweat secretion of sweat glands, the morphology of sweat gland epithelial cells changes accordingly. Under an optical microscope, it can be seen that the sweat gland epithelial cell vacuoles increase in number and expand. Under an electron microscope, such expanded vacuoles appear to be mitochondria in the sweat gland epithelial cell swelling, breakage and fusion and expansion of secretory vesicle. Therefore, through histomorphological observation of sweat gland epithelial tissue of a rat paw, secretory activities of the sweat gland can be known.

300 Wistar rats with equal male and female number, weighing 120~160 g were used. These rats were randomly divided into 30 groups by weight and gender: control groups (0.5% of methyl cellulose), phillygeninin groups, phillyrin groups, low, medium and high dose groups (2.5, 5, 10 mg/kg) of phillyrin/phillygeninin compositions A and B separately, and positive drug pilocarpine groups (35 mg/kg). Each group has 10 rats, the test is repeated 3 times for each group. Pilocarpine solution was administered by subcutaneous injection, the remaining groups were subjected to intragastric administration. After administration of the 0.5% of methyl cellulose in the control group for one hour, after administration of the pilocarpine in the positive drug group for 30 min, and after administration of the phillyrin, the phillygeninin and the phillyrin/phillygeninin composition for one hour, the right hind limb was instantly cut off at the ankle joint to immediately take down the footpad of the right hind limb and placed into 10% of formaldehyde solution.

The footpads were fixed, dehydrated, embedded, sliced and stained with HE by using conventional methods. Changes in sweat gland epithelial cells of the rat paws from each group were observed under an optical microscope, to mainly observe the percentage of vacuolization. The differences among the various groups was performed through $X^2$ test for statistical analysis. The above test was repeated 3 times.

Percentage of vacuolization=(the number of vacuolized sweat glands)/(the number of sweat glands observed)×100%.

(2) Results

Compared with the control group, extremely significant promoting effect was observed on the sweat secretion of the rat paws (p<0.001) of the 2.5, 5, 10 mg/kg groups of the phillyrin/phillygeninin compositions A and B. The low, medium and high dose groups (2.5, 5, 10 mg/kg) of the phillyrin/phillygeninin compositions have significantly better therapeutic effects than the phillyrin and the phillygeninin (p<0.001 or p<0.01). This demonstrated that the phillyrin/phillygeninin compositions have synergetic effects. See Table 2-6 for the details of test results.

TABLE 2-6

Effects of the phillyrin/phillygeninin composition on the sweat secretion of the rat paws (histomorphological observation method, n = 3)

| Groups | Animal number | Number of sweat glands observed | Number of sweat glands of vacuole | percentage of vacuolization (%) |
|---|---|---|---|---|
| Control group | 10 | 242 | 14 | 5.78 |
| Phillyrin | 10 | 209 | 86 | 22.15** |
| Phillygeninin | 10 | 212 | 79 | 20.26** |
| Pilocarpine (35.0 mg/kg) | 10 | 208 | 57 | 27.40*** |
| Phillyrin/phillygeninin composition A | | | | |
| 2.5 mg/kg | 10 | 221 | 25 | 30.31***##▲▲ |
| 5.0 mg/kg | 10 | 213 | 73 | 34.27***###▲▲▲ |
| 10.0 mg/kg | 10 | 207 | 85 | 41.63***###▲▲▲ |
| Phillyrin/phillygeninin composition B | | | | |
| 2.5 mg/kg | 10 | 225 | 66 | 29.30***##▲▲ |
| 5.0 mg/kg | 10 | 219 | 69 | 31.51***###▲▲▲ |
| 10.0 mg/kg | 10 | 208 | 85 | 40.86***###▲▲▲ | compared with the viral control group, p<0.01, *p<0.001; when the phillyrin/phillygeninin composition was compared with the phillyrin, ##p<0.01, ###p<0.001; when the phillyrin/phillygeninin composition was compared with the phillygeninin, ▲▲p<0.01, ▲▲▲p<0.001.

2.3 Effects of the Phillyrin/Phillygeninin Composition on Rat Fever Induced by Beer Yeast (*Saccharomyces cerevisiae*)

(1) Materials and Methods

Male Wistar rats with a weight of 180~200 g were used. Normal anal temperature of each rat was measured twice (at a certain interval) with a WSC-411P portable digital thermometer, and a mean of the two measurement values was taken as a normal body temperature of the rat. Then, 300 rats with body temperature at 36.5~38° C. were selected and randomly divided into 30 groups by weight: model groups (0.5% methyl cellulose), phillyrin/phillygeninin compositions A and B that are divided into low, medium and high dose groups (2.5, 5, 10 mg/kg) respectively, phillyrin groups (13 mg/kg), phillygeninin groups (13 mg/kg), and positive drug paracetamol groups (100 mg/kg). Each group has 10 rates, and the test is repeated 3 times for each group. 10 mL/kg of 10% fresh *Saccharomyces cerevisiae* suspension was subcutaneously injected to the back of the rats of each group to induce fever. After administration of 10% fresh *Saccharomyces cerevisiae* suspension for 6.0 h, the phillyrin/phillygeninin composition and the paracetamol positive drug were administered by intragastric administration, and the same volume of 0.5% methyl cellulose is administrated to the model group by intragastric administration. Rectal temperatures were respectively measured at 1, 2, 3 and 4 h after the administration. Changes in the body temperature were observed and difference between the groups was compared by inter-group t test processing through antipyretic percentage. The above test was repeated totally 3 times.

Antipyretic percentage =

$$\frac{\text{(Body temperature at a certain time after administration)} - \text{(Body temperature at 6 h after fever induction)}}{\text{(Body temperature at 6 h after fever induction)}} \times 100\%$$

(2) Results

Temperatures of rats in each group all increased about 1.5° C. after subcutaneous administration of 10% fresh *Saccharomyces cerevisiae* suspension for 6 h, and were significantly different from the temperatures before fever induction (p<0.001). This indicated that the beer yeast (*Saccharomyces cerevisiae*) induced fever model for rats was successfully established. Compared with the model group, significant hypothermia effects on rat fever induced by *Saccharomyces cerevisiae* (p<0.05~p<0.001) were observed in the medium and high dose groups of the phillyrin/phillygeninin compositions A and B at 1, 2, 3 and 4 h after administration, as well as the low dosage group at 2, 3 and 4 h after administration. Meanwhile, hypothermia effects of the groups with different doses of the phillyrin/phillygeninin compositions A and B were extremely superior to the effects of the phillyrin and the phillygeninin (p<0.0011 or p<0.01), which indicated that the phillyrin/phillygeninin compositions have obvious synergistic effects. See Table 2-7 for the above test results.

2.4 Effects of the Phillyrin/Phillygeninin Compositions on Rabbit Fever Induced by Typhoid and Paratyphoid Vaccine (1) Materials and Methods Male Japanese big-ear white rabbits with a weight 1.5~2.0 kg were used. Before the test, WSC-411P portable digital thermometer was used to measure the normal rectal temperature twice (with certain interval for each time), and the average value was taken as the normal body temperature of rabbits. Then, 198 rabbits with body temperature at 38~39.6° C. were selected and randomly divided into 33 groups by weight: blank control groups (nortrol saline), model control groups (0.5% methyl cellulose), low, medium and high dose groups (1.25, 2.5, 5 mg/kg) of the phillyrin/phillygeninin compositions A and B, phillyrin groups, phillygeninin groups, and paracetamol positive drug groups (50 mg/kg). Each group has 6 rabbits, and the test was repeated 3 times for each group. Rabbits were fixed into a fixator. The blank control group was intravenously injected with normal saline of 1 ml/kg via the ear margin; The model control group and each drug group were intravenously injected with typhoid and paratyphoid vaccines of 0.8 ml/kg via the ear margin. After the body temperatures of the rabbits increased by 1° C. or more (requiring about 1~1.5 h, and this test was limited to 1 h), the blank control group and the model group were administered intragastrically with 0.5% carboxymethycellulose of 1 ml/kg, and the drug groups were administered intragastrically with phillyrin/phillygeninin compositions and paracetamol respectively.

The rectal temperature was measured after administration for 30, 60, 90, 120, 180 and 240 min to observe the changes in the body temperature, and difference between the groups was compared by inter-group t test processing through antipyretic percentage.

Antipyretic percentage =

$$\frac{\text{(Body temperature at a certain time after administration)} - \text{(Body temperature at 1 h after fever induction)}}{\text{(Body temperature at 1 h after fever induction)}} \times 100\%$$

After intravenous injection with the typhoid and paratyphoid vaccines via the ear margin of rabbits for 1 h, the body temperature rise was about 1° C., which indicated that the typhoid and paratyphoid vaccines could be used to prepare the rabbit fever model. Compared with the blank control group, the body temperatures of rabbits in the model group continuously increased during an observation period of 300 min (p<0.05~p<0.001). Compared with the model group, the high, medium and low dose groups of the phillyrin/phillygeninin compositions A and B after administration for 30~240 min, 60~240 min and 90~240 min had significant hypothermal effects on rabbit fever induced by typhoid and paratyphoid vaccine (p<0.05~p<0.001), and their hypothermal effects were also significantly superior to the effects of the phillyrin group and the phillygeninin group (p<0.01), which indicated that the phillyrin/phillygeninin compositions have obvious synergistic effects. See Table 2-8 for the above result results.

2.5 Effects of the Phillyrin/Phillygeninin Compositions on Rat Paw Swelling Induced by Carrageenin (1) Materials and Methods 70 male Wistar rats with a weight of 120~150 g were adopted and randomly divided into 7 groups by weight: a blank control group (0.5% sodium carboxymethyl cellulose), low, medium and high dose groups (2.5, 5 and 10 mg/kg) of the phillyrin/phillygeninin composition A, a phillyrin group, a phillygeninin group and an aspirin positive drug group (100 mg/kg). Each group has 10 rats. Rats in each group were all administered by subcutaneous injection through the sublingual vein. Normal volume of the right hind paw of each rat in each group was measured in capillary magnification measurement method. In order to avoid errors, the measurement should be carried out in a fixed position and operated by the same person before and after administration. A mean of the two measurement values was taken as the normal volume of the right hind paw of a rat before administration. After administration, rats were immediately subcutaneously injected with 0.1 ml of 1% carrageenin at the right hind paws to induce inflammation. Volumes of the right hind paws of rats at 15, 30, 60, 20, 180, 240, 300 and 360 min after inflammation induction were measured. The difference between the groups was compared by inter-group t test processing through the difference percentage (swelling ratio) of the paw volume before and after the induced rat inflammation.

Swelling percentage (%) =

$$\frac{\text{(Volume of a right hind paw after induced inflammation)} - \text{(Volume of the right hind paw before administration)}}{\text{(Volume of the right hind paw before administration)}} \times 100\%$$

Results

Compared with the blank control group, the high dose group (10 mg/kg) of the phillyrin/phillygeninin compositions within 15~360 min after administration, as well as the medium dose group (5 mg/kg) and the low dose group (2.5 mg/kg) of the phillyrin/phillygeninin compositions within 30~360 min after administration had obvious inhibitory effects on rat paw swelling induced by carrageenan (p<0.05 or p<0.01), and their therapeutic effects were significantly better than the effects of the phillyrin group (10 mg/kg) and the phillygeninin group (10 mg/kg) (p<0.05 or p<0.01); moreover, the therapeutic effects of each dose group of the composition at 60 min and 240 min after administration were significantly better than the effects of the phillygeninin group (p<0.01). The above test results indicated that the combined use of the phillyrin and the phillygeninin in the phillyrin/phillygeninin composition has an obvious synergistic effect (see Table 2-9 for details).

TABLE 2-7

Effects of the phillyrin/phillygeninin compositions on body temperatures of feverish rabbits induced by typhoid and paratyphoid vaccine ($\bar{x} \pm s$, n = 3)

| Groups | Normal | 6 h after fever induction | Body temperature(° C.) Time after administration(h) | |
|---|---|---|---|---|
| | | | 1 | 2 |
| Model control group (%) | 37.72 ± 0.90 | 39.30 ± 0.54<br>4.22 ± 2.11### | 39.44 ± 0.58<br>0.37 ± 1.66 | 39.42 ± 0.47<br>0.31 ± 1.77 |
| Paracetamol | | | | |
| 100 mg/kg (%) | 37.55 ± 0.70 | 39.48 ± 0.62<br>5.14 ± 1.42### | 38.66 ± 0.59<br>−2.07 ± 0.54** | 38.19 ± 0.59<br>−3.27 ± 0.77*** |
| Phillyrin | | | | |
| 10 mg/kg (%) | 37.58 ± 0.59 | 39.53 ± 0.63<br>5.18 ± 1.52### | 39.13 ± 0.52<br>−0.60 ± 0.39 | 38.77 ± 0.42<br>−0.92 ± 0.93** |
| Phillygeninin | | | | |
| 10 mg/kg (%) | 37.50 ± 0.59 | 39.44 ± 0.47<br>5.17 ± 1.37### | 39.31 ± 0.48<br>−0.33 ± 0.41 | 39.04 ± 0.45<br>−0.69 ± 0.93* |

TABLE 2-7-continued

Effects of the phillyrin/phillygeninin compositions on body temperatures of feverish rabbits induced by typhoid and paratyphoid vaccine ($\bar{x} \pm s$, n = 3)

Phillyrin/phillygeninin composition A

| | | | | |
|---|---|---|---|---|
| 2.5 mg/kg | 37.33 ± 0.51 | 39.23 ± 0.63 | 38.86 ± 0.47 | 38.20 ± 0.44 |
| (%) | | 5.10 ± 1.45### | −0.95 ± 1.02▲ | −1.70 ± 1.11▲ |
| 5.0 mg/kg | 37.41 ± 0.55 | 39.37 ± 0.41 | 38.61 ± 0.52 | 38.46 ± 0.55 |
| (%) | | 5.25 ± 1.25### | −1.92 ± 0.42#△▲▲ | −2.31 ± 0.57**△▲ |
| 10.0 mg/kg | 37.53 ± 0.59 | 39.54 ± 0.62 | 38.69 ± 0.57 | 37.72 ± 0.40 |
| (%) | | 5.36 ± 1.52### | −2.16 ± 0.51**△△▲▲ | −2.85 ± 0.93**△▲▲ |

Phillyrin/phillygeninin composition B

| | | | | |
|---|---|---|---|---|
| 2.5 mg/kg | 37.64 ± 0.42 | 39.60 ± 0.63 | 39.26 ± 0.47 | 38.97 ± 0.41 |
| (%) | | 5.21 ± 1.40### | −0.87 ± 1.12▲ | −1.59 ± 1.18▲ |
| 5.0 mg/kg | 37.47 ± 0.63 | 39.47 ± 0.43 | 38.76 ± 0.56 | 38.57 ± 0.52 |
| (%) | | 5.33 ± 1.27### | −1.80 ± 0.50*△▲▲ | −2.27 ± 0.50**△▲ |
| 10.0 mg/kg | 37.55 ± 0.76 | 39.48 ± 0.67 | 38.71 ± 0.49 | 38.39 ± 0.48 |
| (%) | | 5.13 ± 1.50### | −1.95 ± 0.58**△△▲▲ | −2.76 ± 0.85**△▲▲ |

| Groups | Body temperature(° C.) Time after administration(h) | |
|---|---|---|
| | 3 | 4 |
| Model control group | 38.88 ± 0.46 | 38.57 ± 0.49 |
| (%) | −1.07 ± 1.54 | −1.86 ± 1.20 |
| Paracetamol | | |
| 100 mg/kg | 37.98 ± 0.19 | 37.84 ± 0.32 |
| (%) | −3.80 ± 1.43*** | −4.15 ± 1.59*** |
| Phillyrin | | |
| 10 mg/kg | 38.63 ± 0.40 | 38.46 ± 0.31 |
| (%) | −1.29 ± 1.18* | −1.70 ± 1.23* |
| Phillygeninin | | |
| 10 mg/kg | 38.91 ± 0.40 | 38.70 ± 0.31 |
| (%) | −1.03 ± 1.18* | −1.55 ± 1.23* |
| Phillyrin/phillygeninin composition A | | |
| 2.5 mg/kg | 37.85 ± 0.52 | 38.52 ± 0.59 |
| (%) | −2.61 ± 1.65**△▲ | −3.45 ± 1.88**△▲ |
| 5.0 mg/kg | 38.22 ± 0.32 | 37.84 ± 0.41 |
| (%) | −2.93 ± 0.36**△▲ | −3.93 ± 0.50***△△▲▲ |
| 10.0 mg/kg | 37.27 ± 0.42 | 37.08 ± 0.35 |
| (%) | −3.66 ± 1.18***△△▲▲ | −4.16 ± 1.23***△△▲▲ |
| Phillyrin/phillygeninin composition B | | |
| 2.5 mg/kg | 38.59 ± 0.35 | 38.30 ± 0.50 |
| (%) | −2.54 ± 1.32**△▲ | −3.29 ± 1.81***△▲ |
| 5.0 mg/kg | 38.35 ± 0.40 | 37.95 ± 0.38 |
| (%) | −2.84 ± 0.31**△▲ | −3.85 ± 0.44***△△▲▲ |
| 10.0 mg/kg | 38.24 ± 0.37 | 37.90 ± 0.31 |
| (%) | −3.15 ± 1.10***△△▲▲ | −4.00 ± 1.12***△△▲▲ |

When compared with the model control group, *$p<0.05$; $p<0.01$; *$p<0.001$;
when compared with normal group (before fever induction), ####$p<0.001$. When the antipyretic percentage of the phillyrin/phillygeninin composition was compared with that of the phillyrin, △$p<0.05$; △△$p<0.01$; △△△$p<0.001$; when the antipyretic percentage of the phillyrin/phillygeninin composition was compared with that of the phillygeninin, ▲$p<0.05$; ▲▲$p<0.01$; ▲▲▲$p<0.001$.

TABLE 2-8

Effects of the phillyrin/phillygeninin compositions on body temperatures of feverish rabbits induced by typhoid and paratyphoid vaccine ($\bar{x} \pm s$, n = 3)

| Groups | Normal | 1 h after fever induction | Body temperature (° C.) Time after administration (min) | | |
|---|---|---|---|---|---|
| | | | 30 | 60 | 90 |
| Blank control group (%) | 39.47 ± 0.25 | 39.50 ± 0.21 0.15 ± 0.25 | 39.56 ± 0.24 0.15 ± 0.25 | 39.45 ± 0.20 −0.13 ± 0.15 | 39.54 ± 0.22 0.11 ± 0.14 |

TABLE 2-8-continued

Effects of the phillyrin/phillygeninin compositions on body temperatures of feverish rabbits induced by typhoid and paratyphoid vaccine ($\bar{x} \pm s$, n = 3)

| | | | | | |
|---|---|---|---|---|---|
| Model ontrol group (%) | 39.68 ± 0.54 | 41.10 ± 0.51### <br> 3.60 ± 1.03 | 41.23 ± 0.52 <br> 0.32 ± 0.28 | 41.27 ± 0.52## <br> 0.41 ± 0.19 | 41.22 ± 0.52* <br> 0.28 ± 0.15 |
| | | | Paracetamol | | |
| 50 mg/kg (%) | 39.53 ± 0.49 | 40.09 ± 0.41### <br> 3.71 ± 0.27 | 40.53 ± 0.65** <br> −1.14 ± 0.56 | 40.10 ± 0.49*** <br> −2.18 ± 0.17 | 39.83 ± 0.58*** <br> −2.83 ± 0.15 |
| | | | Phillyrin | | |
| 5.2 mg/kg (%) | 39.59 ± 0.30 | 40.98 ± 0.23### <br> 3.52 ± 0.41 | 40.83 ± 0.26 <br> −0.37 ± 0.15 | 40.58 ± 0.21 <br> −0.61 ± 0.12 | 40.43 ± 0.22 <br> −0.97 ± 0.27 |
| | | | Phillygeninin | | |
| 5.2 mg/kg (%) | 39.63 ± 0.30 | 41.10 ± 0.24### <br> 3.71 ± 0.41 | 41.06 ± 0.26 <br> −0.10 ± 0.11 | 40.86 ± 0.21 <br> −0.49 ± 0.10 | 40.74 ± 0.22 <br> −0.77 ± 0.22 |
| | | | Phillyrin/phillygeninin composition A | | |
| 1.3 mg/kg (%) | 39.56 ± 0.21 | 41.13 ± 0.47### <br> 3.99 ± 0.52 | 41.94 ± 0.49 <br> −0.46 ± 0.18 | 41.52 ± 0.42 <br> −0.90 ± 0.12 | 41.36 ± 0.33 <br> −1.29 ± 0.27**△△▲▲ |
| 2.6 mg/kg (%) | 39.72 ± 0.29 | 41.23 ± 0.35### <br> 3.79 ± 0.46 | 40.88 ± 0.32 <br> −0.85 ± 0.02 | 40.43 ± 0.38 <br> −1.09 ± 0.03**△△▲▲ | 40.21 ± 0.23 <br> −1.65 ± 0.19**△△▲▲ |
| 5.2 mg/kg (%) | 39.77 ± 0.30 | 41.17 ± 0.23### <br> 3.51 ± 0.41 | 40.75 ± 0.26 <br> −1.02 ± 0.15**△△▲▲ | 40.03 ± 0.21 <br> −1.77 ± 0.12**△△▲▲ | 39.85 ± 0.22 <br> −2.21 ± 0.27***△△▲▲ |
| | | | Phillyrin/phillygeninin composition B | | |
| 1.3 mg/kg (%) | 39.56 ± 0.32 | 41.15 ± 0.39### <br> 4.02 ± 0.44 | 39.44 ± 0.46 <br> −0.29 ± 0.10 | 39.85 ± 0.36 <br> −0.73 ± 0.20 | 39.94 ± 0.35 <br> −0.95 ± 0.29**▲▲ |
| 2.6 mg/kg (%) | 39.72 ± 0.25 | 41.24 ± 0.40### <br> 3.83 ± 0.41 | 39.50 ± 0.38 <br> −0.55 ± 0.17 | 39.40 ± 0.31 <br> −0.81 ± 0.09**△▲▲ | 39.20 ± 0.32 <br> −1.30 ± 0.20**△▲▲ |
| 5.2 mg/kg (%) | 39.77 ± 0.33 | 41.16 ± 0.21### <br> 3.51 ± 0.32 | 39.40 ± 0.19 <br> −0.94 ± 0.23**△▲▲ | 39.16 ± 0.34 <br> −1.52 ± 0.20**△▲▲ | 38.97 ± 0.24 <br> −2.00 ± 0.21***△▲▲ |

| | Body temperature (° C.) Time after administration (min) | | |
|---|---|---|---|
| Groups | 120 | 180 | 240 |
| Blank control group (%) | 39.49 ± 0.23 <br> −0.02 ± 0.10 | 39.56 ± 0.27 <br> 0.15 ± 0.24 | 39.59 ± 0.26 <br> 0.23 ± 0.08 |
| Model ontrol group (%) | 41.21 ± 0.51* <br> 0.26 ± 0.29 | 40.95 ± 0.48## <br> −0.36 ± 0.22 | 40.49 ± 0.57### <br> −1.48 ± 0.25 |
| Paracetamol | | | |
| 50 mg/kg (%) | 39.72 ± 0.56*** <br> −3.11 ± 0.20 | 39.61 ± 0.41*** <br> −3.38 ± 0.22 | 39.53 ± 0.47*** <br> −3.58 ± 0.38 |
| Phillyrin | | | |
| 5.2 mg/kg (%) | 40.37 ± 0.27 <br> −1.13 ± 0.14** | 40.16 ± 0.23 <br> −1.65 ± 0.12** | 39.92 ± 0.25 <br> −2.22 ± 0.11*** |
| Phillygeninin | | | |
| 5.2 mg/kg (%) | 40.65 ± 0.27 <br> −1.00 ± 0.18** | 40.49 ± 0.23 <br> −1.39 ± 0.17** | 40.30 ± 0.25 <br> −1.85 ± 0.15** |
| Phillyrin/phillygeninin composition A | | | |
| 1.3 mg/kg (%) | 41.13 ± 0.46 <br> −1.83 ± 0.34** | 40.94 ± 0.33 <br> −2.30 ± 0.46***△△▲▲ | 40.61 ± 0.31 <br> −3.08 ± 0.25***△△▲▲ |
| 2.6 mg/kg (%) | 39.94 ± 0.25 <br> −2.30 ± 0.44***△△▲▲ | 39.73 ± 0.26 <br> −2.82 ± 0.22***△△▲▲ | 39.35 ± 0.22 <br> −3.75 ± 0.31***△△▲▲ |
| 5.2 mg/kg (%) | 39.58 ± 0.27 <br> −2.93 ± 0.14***△△▲▲ | 39.32 ± 0.23 <br> −3.50 ± 0.12***△△▲▲ | 38.99 ± 0.25 <br> −4.33 ± 0.11***△△▲▲ |
| Phillyrin/phillygeninin composition B | | | |
| 1.3 mg/kg (%) | 38.95 ± 0.49 <br> −1.53 ± 0.30** | 38.76 ± 0.29 <br> −2.02 ± 0.30***△△▲▲ | 39.25 ± 0.20 <br> −0.78 ± 0.41***△△▲▲ |
| 2.6 mg/kg (%) | 38.92 ± 0.29 <br> −2.01 ± 0.44**△▲▲ | 38.71 ± 0.12 <br> −2.54 ± 0.37***△▲▲ | 38.48 ± 0.32 <br> −3.11 ± 0.24***△▲▲ |
| 5.2 mg/kg (%) | 38.75 ± 0.25 <br> −2.56 ± 0.20***△▲▲ | 38.54 ± 0.26 <br> −3.10 ± 0.18***△▲▲ | 38.19 ± 0.11 <br> −3.97 ± 0.09***△▲▲ |

When compared with the model control group, *p<0.05; p<0.01; *p<0.001; when compared with normal group (before fever induction), ###p<0.001.

When the antipyretic percentage of the phillyrin/phillygeninin composition was compared with that of the phillyrin, ᐃp<0.05; ᐃᐃp<0.01. When the antipyretic percentage of the phillyrin/phillygeninin composition was compared with that of the phillygeninin, ▲p<0.05; ▲▲p<0.01.

TABLE 2-9

Inhibitory effects of the phillyrin/phillygeninin compositions on rat paw swelling induced by carrageenan ($\bar{x} \pm s$, n = 10)

| Groups | Swelling percentage (%) | | | | |
|---|---|---|---|---|---|
| | 15 min | 30 min | 60 min | 120 min | 180 min |
| Control group | 18.7 ± 12.6 | 28.9 ± 14.6 | 33.8 ± 10.5 | 46.5 ± 18.2 | 46.7 ± 15.3 |
| Aspirin | | | | | |
| 100 mg/kg | 8.90 ± 6.70* | 15.6 ± 12.2* | 20.3 ± 10.9* | 21.6 ± 12.1** | 26.1 ± 21.1** |
| Phillyrin | | | | | |
| 10.0 mg/kg | 12.9 ± 8.41 | 19.9 ± 9.55 | 21.8 ± 11.8* | 28.9 ± 14.0* | 30.8 ± 15.4* |
| Phillygeninin | | | | | |
| 10.0 mg/kg | 14.9 ± 6.13 | 21.9 ± 9.72 | 27.1 ± 13.5 | 30.7 ± 10.2* | 33.8 ± 12.1* |
| Phillyrin/phillygeninin composition A | | | | | |
| 2.5 mg/kg | 13.6 ± 8.40 | 24.2 ± 16.3 | 20.1 ± 14.8*▲▲ | 22.0 ± 16.0ᐃ▲ | 26.8 ± 16.1ᐃ▲ |
| 5.0 mg/kg | 11.4 ± 8.90 | 15.2 ± 6.20*ᐃ▲ | 18.0 ± 9.00*▲▲ | 19.7 ± 12.1ᐃ▲ | 22.0 ± 14.9ᐃ▲ |
| 10.0 mg/kg | 9.0 ± 7.90*ᐃ▲ | 13.2 ± 9.50*ᐃ▲ | 15.8 ± 11.6ᐃ▲▲ | 17.9 ± 14.3ᐃ▲ | 19.7 ± 15.2**ᐃ▲ |
| Phillyrin/phillygeninin composition B | | | | | |
| 2.5 mg/kg | 13.5 ± 8.52 | 24.9 ± 16.0 | 21.1 ± 14.1*▲▲ | 23.1 ± 16.5ᐃ▲ | 27.4 ± 15.6ᐃ▲ |
| 5.0 mg/kg | 12.4 ± 8.71 | 16.0 ± 6.15*ᐃ▲ | 19.5 ± 9.55*▲▲ | 20.2 ± 11.6ᐃ▲ | 23.2 ± 15.2ᐃ▲ |
| 10.0 mg/kg | 9.9 ± 7.80*ᐃ▲ | 13.9 ± 9.61*ᐃ▲ | 16.9 ± 12.2ᐃ▲▲ | 18.2 ± 14.8ᐃ▲ | 20.5 ± 15.9**ᐃ▲ |

| Groups | Swelling percentage (%) | | |
|---|---|---|---|
| | 240 min | 300 min | 360 min |
| Control group | 48.8 ± 21.9 | 49.1 ± 14.6 | 47.4 ± 15.5 |
| Aspirin | | | |
| 100 mg/kg | 26.1 ± 16.3** | 34.9 ± 14.6* | 31.9 ± 12.2* |
| Phillyrin | | | |
| 10.0 mg/kg | 29.9 ± 11.1* | 33.5 ± 10.0* | 32.2 ± 11.9* |
| Phillygeninin | | | |
| 10.0 mg/kg | 31.0 ± 11.3* | 35.8 ± 13.5* | 36.4 ± 10.2 |
| Phillyrin/phillygeninin composition A | | | |
| 2.5 mg/kg | 26.8 ± 23.3ᐃ▲ | 29.5 ± 16.1ᐃ▲ | 32.4 ± 23.4*▲▲ |
| 5.0 mg/kg | 24.2 ± 12.0ᐃ▲ | 27.8 ± 13.1ᐃ▲ | 30.0 ± 16.0**ᐃ▲ |
| 10.0 mg/kg | 22.5 ± 11.8ᐃ▲ | 25.4 ± 10.6ᐃ▲ | 28.7 ± 11.4**ᐃ▲ |
| Phillyrin/phillygeninin composition B | | | |
| 2.5 mg/kg | 27.7 ± 23.7ᐃ▲ | 30.4 ± 16.9ᐃ▲ | 33.1 ± 22.8*▲▲ |
| 5.0 mg/kg | 25.6 ± 11.6ᐃ▲ | 28.89 ± 12.7ᐃ▲ | 31.6 ± 15.5**ᐃ▲ |
| 10.0 mg/kg | 23.8 ± 12.0ᐃ▲ | 26.1 ± 11.3ᐃ▲ | 29.8 ± 11.9**ᐃ▲ |

When compared with the control group, *p<0.05; **p<0.01;

when the antipyretic percentage of the phillyrin/phillygeninin composition was compared with that of the phillyrin, ᐃp<0.05; ᐃᐃp<0.01; when the antipyretic percentage of the phillyrin/phillygeninin composition was compared with that of the phillygeninin, ▲p<0.05; ▲▲p<0.01.

The invention claimed is:

1. A method of alleviating or/and treating a viral disease, which comprises the step of administrating an effective amount of a pharmaceutical composition for alleviating or/and treating a viral disease to a patient in need, wherein the pharmaceutical composition consisting of phillyrin, phillygeninin and a pharmaceutically acceptable carrier, the ratio of phillyrin to phillygeninin in parts by weight is 80-98:2-20, the viral disease is caused by a virus selected from the group consisting of influenza viruses, parainfluenza viruses, Coxsackie virus CoxA16, respiratory syncytial viruses, herpes zoster simplex virus HSV-I, herpes zoster simplex virus HSV-II, herpes zoster simplex virus CVB3, adenovirus and enterovirus EV71, and the pharmaceutical composition contains no other antivirus components extracted from *Forsythia suspense*.

2. The method of claim 1, wherein the ratio of phillyrin to phillygeninin in parts by weight is 90-98:2-10.

3. The method of claim 1, wherein the ratio of the total weight of phillyrin and phillygeninin in the pharmaceutical composition to the weight of the pharmaceutically acceptable carrier is 1:1 to 1:100.

4. The method of claim 1, wherein the pharmaceutically acceptable carrier is cyclodextrin.

5. The method of claim 1, wherein the pharmaceutically acceptable carrier is α-cyclodextrin, β-cyclodextrin or γ-cyclodextrin.

6. The method of claim 1, wherein the pharmaceutical composition exists in a form selected from the group consisting of a tablet, capsule, pill, powder, granule, syrup, solution, emulsion, injection, spray, aerosol, gel, cream, cataplasm, rubber plaster and patch.

* * * * *

UNITED STATES PATENT AND TRADEMARK OFFICE
CERTIFICATE OF CORRECTION

PATENT NO. : 10,286,002 B2
APPLICATION NO. : 15/502000
DATED : May 14, 2019
INVENTOR(S) : Li Fu et al.

It is certified that error appears in the above-identified patent and that said Letters Patent is hereby corrected as shown below:

In the Specification

Column 21, Line 15, delete "degreased" and insert --decreased--.

Column 39, Table 2-8, Line 10, delete "ontrol" and insert --control--.

Signed and Sealed this
Nineteenth Day of November, 2019

Andrei Iancu
*Director of the United States Patent and Trademark Office*